US009877683B2

(12) United States Patent
Takahashi et al.

(10) Patent No.: US 9,877,683 B2
(45) Date of Patent: Jan. 30, 2018

(54) ACTIVITY STATE INFORMATION DETECTING DEVICE AND METHOD FOR CONTROLLING ACTIVITY STATE INFORMATION DETECTING DEVICE

(71) Applicant: SEIKO EPSON CORPORATION, Tokyo (JP)

(72) Inventors: Yusuke Takahashi, Matsumoto (JP); Hidenori Nakamura, Shimosuwa-machi (JP)

(73) Assignee: SEIKO EPSON CORPORATION, Tokyo (JP)

( * ) Notice: Subject to any disclaimer, the term of this patent is extended or adjusted under 35 U.S.C. 154(b) by 14 days.

(21) Appl. No.: 14/871,389

(22) Filed: Sep. 30, 2015

(65) Prior Publication Data

US 2016/0098081 A1 Apr. 7, 2016

(30) Foreign Application Priority Data

Oct. 1, 2014 (JP) .................................. 2014-203097

(51) Int. Cl.

| G06F 3/01 | (2006.01) |
|---|---|
| G06F 1/16 | (2006.01) |
| A61B 5/00 | (2006.01) |
| G04G 21/02 | (2010.01) |
| G06F 1/32 | (2006.01) |
| A61B 5/024 | (2006.01) |

(52) U.S. Cl.
CPC ........... *A61B 5/681* (2013.01); *G04G 21/025* (2013.01); *G06F 1/163* (2013.01); *G06F 1/1694* (2013.01); *G06F 1/1698* (2013.01); *G06F 1/3215* (2013.01); *G06F 3/011* (2013.01); *A61B 5/02438* (2013.01)

(58) Field of Classification Search
CPC ...... G06F 3/011; G06F 1/3215; G06F 1/1694; G06F 1/1698; G06F 1/163; A61B 5/681; A61B 5/0245; A61B 5/02055; A61B 5/0205; A61B 5/02; A61B 5/0031; A61B 5/02438; G04G 21/025
USPC ................................. 340/5.51; 600/483, 503
See application file for complete search history.

(56) References Cited

U.S. PATENT DOCUMENTS 5,759,156 A * 6/1998 Hayakawa ......... A61B 5/02438
600/483
6,999,685 B1 * 2/2006 Kawase ............... A61B 5/0031
398/129

(Continued)

FOREIGN PATENT DOCUMENTS

| JP | 2006-141902 A | 6/2006 |
|---|---|---|
| JP | 2008-061663 A | 3/2008 |

*Primary Examiner* — Ali Neyzari
(74) *Attorney, Agent, or Firm* — Maschoff Brennan

(57) ABSTRACT

An activity state information detecting device includes: a pulse wave measuring section that measures pulse wave information of a user; a body motion measuring section that measures body motion information of the user; and a processing section that performs a calculation process of activity state information of the user, in which the processing section performs a mode switching process between a first mode for performing the calculation process of the activity state information based on the body motion information and a second mode for performing the calculation process of the activity state information based on the pulse wave information.

15 Claims, 11 Drawing Sheets

(56) References Cited

U.S. PATENT DOCUMENTS

| | | | |
|---|---|---|---|
| 7,018,338 B2* | 3/2006 | Vetter | A61B 5/721 |
| | | | 600/479 |
| 8,303,512 B2* | 11/2012 | Kosuda | A61B 5/02 |
| | | | 600/500 |
| 2004/0186387 A1* | 9/2004 | Kosuda | A61B 5/02 |
| | | | 600/502 |
| 2008/0005861 A1 | 1/2008 | Niizaki et al. | |
| 2012/0157860 A1* | 6/2012 | Suzuki | A61B 5/0205 |
| | | | 600/484 |
| 2015/0362977 A1* | 12/2015 | Doniwa | G06F 1/3231 |
| | | | 713/324 |
| 2016/0007916 A1* | 1/2016 | Iwawaki | A61B 5/02055 |
| | | | 600/301 |
| 2016/0360972 A1* | 12/2016 | Kusakabe | A61B 5/0245 |

* cited by examiner

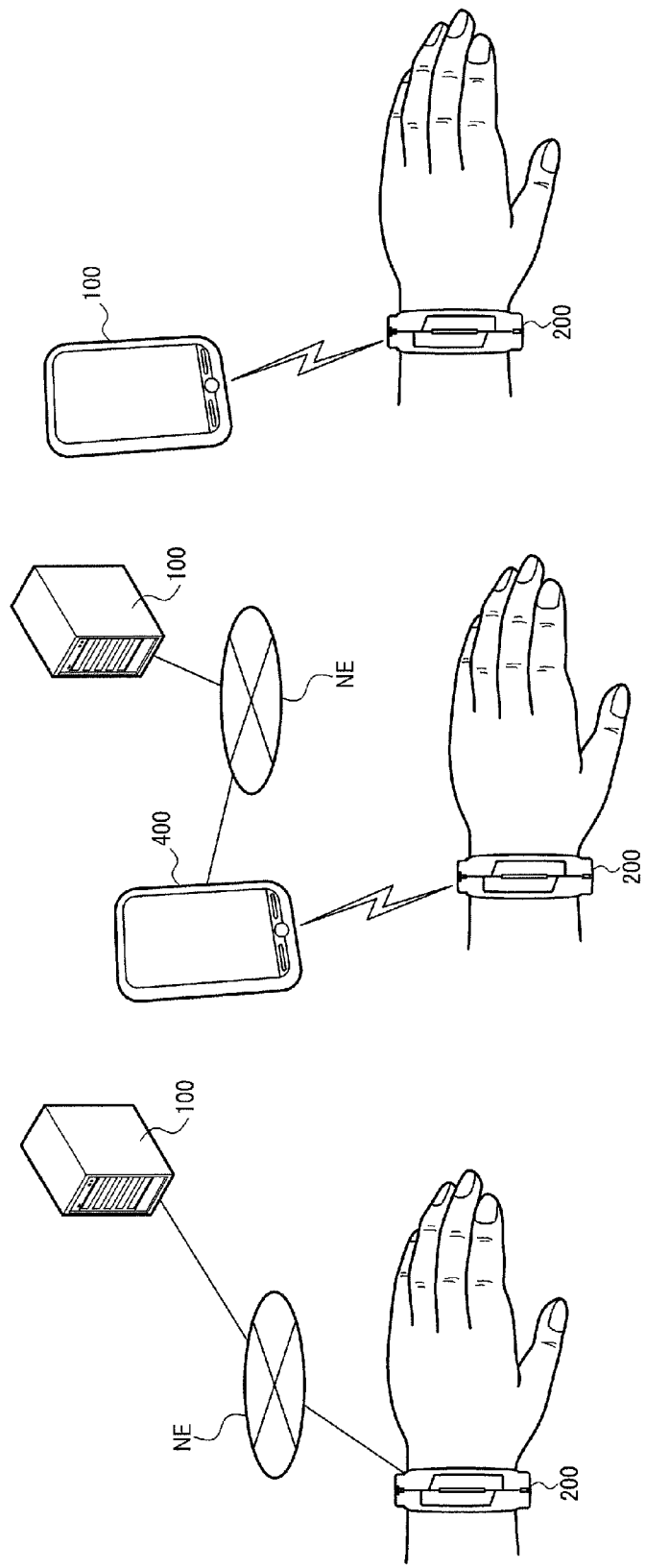

FIG. 6A

| SCHEDULE NO. | START DATE | START TIMING | END DATE | END TIMING |
|---|---|---|---|---|
| DATE001 | 2014/07/19 | 06:00:00 | 2014/07/19 | 08:00:00 |
| DATE002 | 2014/07/23 | 18:00:00 | 2014/07/23 | 19:00:00 |
| DATE003 | 2014/07/26 | 06:00:00 | 2014/07/26 | 08:00:00 |

FIG. 6B

| SCHEDULE NO. | DAY OF WEEK | START TIMING | END TIMING |
|---|---|---|---|
| WEEK001 | SUNDAY | 06:00:00 | 08:00:00 |
| WEEK002 | FRIDAY | 18:00:00 | 19:00:00 |
| WEEK003 | – | 06:00:00 | 08:00:00 |

ACTIVITY STATE INFORMATION DETECTING DEVICE AND METHOD FOR CONTROLLING ACTIVITY STATE INFORMATION DETECTING DEVICE

This application claims priority to Japanese Patent Application No. 2014-203097, filed Oct. 1, 2014, the entirety of which is hereby incorporated by reference.

BACKGROUND

1. Technical Field

The present invention relates to an activity state information detecting device, a method for controlling the activity state information detecting device, and the like.

2. Related Art

In the related art, a device that is provided with various sensors such as an acceleration sensor and is capable of acquiring information indicating an activity state of a user (a physical activity meter in a narrow sense) by being continuously worn by the user is known. In such a device, considering that it is necessary to detect the user's state by the sensors, the device may be realized as a wearable device to be mounted by a user, for example.

Further, as the physical activity meter, there is a physical activity meter mounted by a user for a relatively short time (about several hours at the longest) during exercise in consideration of only an exercise state as an activity state of the user, but as easily understood in consideration of a pedometer which has been widely used, there is also a physical activity meter mounted by a user for a relatively long period of time (24 hours or the like).

For example, the physical activity meter realized as the wearable device or the like may be driven by a battery. Here, in a device in which only a body motion sensor such as an acceleration sensor is mounted, power consumption does not matter. However, in recent years, it is also considered that a pulse wave sensor is included in the physical activity meter. Since the pulse wave sensor causes large power consumption compared to the body motion sensor, it is necessary to perform an efficient operation for the realization of continuous driving for a long period of time as described above.

For example, JP-A-2008-61663 discloses a technique for determining a biologic state based on measured biologic information and suppressing power consumption based on the determination result, in a device that acquires pulse wave information.

A variety of information is included in activity state information indicating a user's activity state. For example, the activity state information may include calorie consumption information, step number information, movement speed information, movement path information (which will be described later), and the like, for example. Further, when various sensors are included in a device (activity state information detecting device), a situation where predetermined activity state information can be calculated from an output of a first sensor and can be calculated from an output of a second sensor may be considered.

In such a situation, which sensor information is preferably used for the calculation of activity state information may be changed according to a characteristic of each sensor or a user's state. However, the related art technique disclosed in JP-A-2008-61663 or the like does not disclose a technique for automatically switching a mode for calculating this activity state information based on a sensor output. Particularly, in a device capable of acquiring pulse wave information from a pulse wave sensor, a technique for performing switching of whether to calculate activity state information from pulse wave information or calculate the activity state information from another sensor's information is not disclosed.

SUMMARY

An advantage of some aspects of the invention is to provide an activity state information detecting device which is efficiently operated by appropriately switching a mode for calculating activity state information based on pulse wave information and a mode for calculating the activity state information based on body motion information, a method for controlling the activity state information detecting device, and the like.

An aspect of the invention relates to an activity state information detecting device including a pulse wave measuring section that measures pulse wave information of a user; a body motion measuring section that measures body motion information of the user; and a processing section that performs a calculation process of activity state information of the user, in which the processing section performs a mode switching process between a first mode for performing the calculation process of the activity state information based on the body motion information and a second mode for performing the calculation process of the activity state information based on the pulse wave information.

In the aspect of the invention, in the device capable of measuring the pulse wave information and the body motion information, the switching of whether the pulse wave information or the body motion information is used in a calculation process of predetermined activity state information is performed. Thus, it is possible to use appropriate information among the pulse wave information and the body motion information in calculation of the activity state information according to various situations, and thus, it is possible to efficiently operate the activity state information detecting device so that the measurement of the pulse wave information is set to OFF in the first mode, for example.

In the aspect of the invention, the processing section may perform the mode switching process based on an amount of remaining battery.

According to this configuration, it is possible to perform the mode switching process based on the amount of remaining battery.

In the aspect of the invention, the processing section may set the second mode when the amount of remaining battery is equal to or greater than a predetermined threshold value, and may set the first mode or the second mode when the amount of remaining battery is smaller than the predetermined threshold value.

According to this configuration, it is possible to perform the mode switching process based on comparison processing of the amount of remaining battery and the predetermined threshold value.

In the aspect of the invention, when the amount of remaining battery is smaller than the predetermined threshold value, and when it is determined that the user is in an exercise state or a sleep state based on the body motion information, the processing section may set the second mode.

According to this configuration, it is possible to perform the mode switching process based on the comparison processing of the amount of remaining battery and the predetermined threshold value and a user behavior determination process, for example.

In the aspect of the invention, when the amount of remaining battery is smaller than the predetermined threshold value, and when it is determined that the user is in a resting state based on the body motion information, the processing section may set the first mode.

According to this configuration, it is possible to perform the mode switching process based on the comparison processing of the amount of remaining battery and the predetermined threshold value and a user behavior determination process, for example.

In the aspect of the invention, when it is determined that the user is in an exercise state or a sleep state based on the body motion information, the processing section may set the second mode.

According to this configuration, it is possible to perform the mode switching process based on a user behavior determination process, for example.

In the aspect of the invention, when it is determined that the user is in a resting state based on the body motion information, the processing section may set the first mode.

According to this configuration, it is possible to perform the mode switching process based on a user behavior determination process, for example.

In the aspect of the invention, the processing section may perform the mode switching process based on at least one of schedule information and timing information.

According to this configuration, it is possible to perform the mode switching process based on the schedule information and the timing information, for example.

In the aspect of the invention, when it is determined that the user is in an exercise state or a sleep state based on at least one of the schedule information and the timing information, the processing section may set the second mode.

According to this configuration, it is possible to perform the mode switching process based on a user behavior determination process using the schedule information and the timing information, for example.

In the aspect of the invention, the activity state information detecting device may further include a position information acquiring section that acquires position information of the user, and the processing section may perform the mode switching process based on the position information.

According to this configuration, it is possible to perform the mode switching process based on the position information, for example.

In the aspect of the invention, when it is determined that the user is in an exercise state based on the position information, the processing section may set the second mode.

According to this configuration, it is possible to perform the mode switching process based on a user behavior determination process using the position information, for example.

In the aspect of the invention, the processing section may calculate calorie consumption information as the activity state information based on the body motion information in the first mode, and may calculate the calorie consumption information as the activity state information based on the pulse wave information in the second mode.

According to this configuration, it is possible to calculate the calorie consumption information of the user as the activity state information.

In the aspect of the invention, the processing section may calculate speed information of the user based on the body motion information in the first mode, and may calculate the calorie consumption information from the speed information.

According to this configuration, it is possible to calculate the speed information from the body motion information in the first mode to calculate the calorie consumption information.

In the aspect of the invention, the processing section may calculate step number information of the user based on acceleration information which is the body motion information in the first mode, may calculate the speed information of the user based on the step number information, and may calculate the calorie consumption information as the activity state information from the speed information.

According to this configuration, it is possible to use the acceleration information as the body motion information in the first mode, and to perform a process of calculating the step number information from the acceleration information, a process of calculating the speed information from the step number information, and a process of calculating the calorie consumption information from the speed information.

Another aspect of the invention relates to a method for controlling an activity state information detecting device, the method including: measuring pulse wave information of a user; measuring body motion information of the user; performing a mode switching process between a first mode for performing the calculation process of activity state information based on the body motion information and a second mode for performing the calculation process of the activity state information based on the pulse wave information; and performing a calculation process of the activity state information in a mode set in the mode switching process.

BRIEF DESCRIPTION OF THE DRAWINGS

The invention will be described with reference to the accompanying drawings, wherein like numbers reference like elements.

FIGS. 5A to 5C are diagrams illustrating a specific configuration example of a system including an activity state information detecting device.

FIGS. 6A and 6B are diagrams illustrating a specific example of schedule information.

DESCRIPTION OF EXEMPLARY EMBODIMENTS

Figure 1:
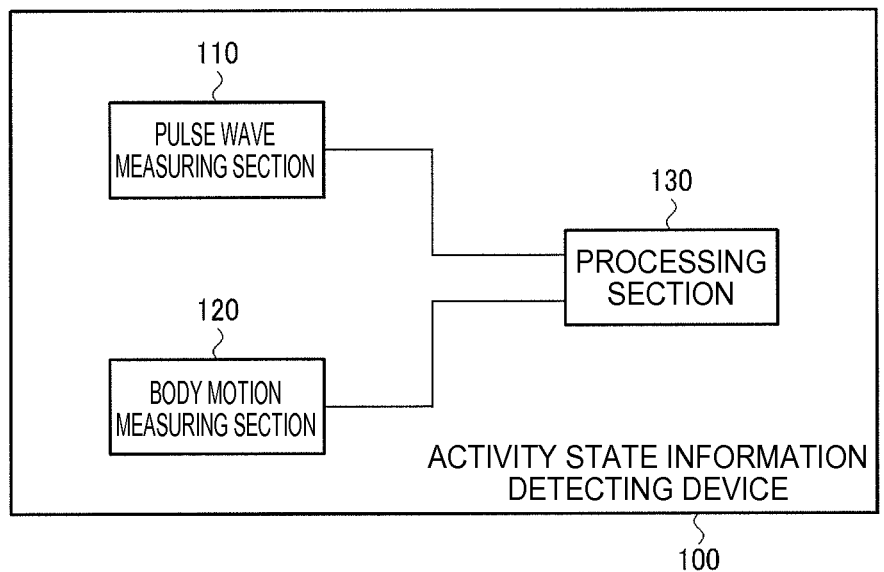
FIG. 1 is a diagram illustrating a configuration example of an activity state information detecting device.

Hereinafter, preferred embodiments of the invention will be described. The following embodiments do not improperly limit the content of the invention disclosed in the appended claims. Further, all configurations described in the embodiments are not essential elements of the invention.

1. Technique of Present Embodiment

First, a technique of the present embodiment will be described. As described above, an activity information detecting device (a physical activity meter) that is provided with various sensors such as an acceleration sensor and is capable of acquiring information indicating an activity state of a user by being continuously worn by the user is known.

Further, in recent years, a device that includes a pulse wave sensor and is capable of acquiring pulse wave information has also been used. The pulse wave sensor is a sensor for detecting a pulse wave signal, and may employ a photoelectric sensor that includes a light emitting section and a light receiving section, for example. In addition, it is known that the pulse wave sensor may be realized by various sensors such as other types of sensors (for example, an ultrasonic sensor), and the pulse wave sensor according to the present embodiment may widely employ these sensors.

No matter which type of pulse wave sensor is used, it is common that the power consumption of the pulse wave sensor is larger than that of a body motion sensor that acquires body motion information. The body motion sensor may employ various sensors such as an acceleration sensor, a gyro sensor, a direction sensor, or an atmospheric pressure sensor. Hereinafter, for simplification of description, the body motion sensor is described as an acceleration sensor, but may be a sensor for detecting other body motions.

For example, when the photoelectric sensor is used as the pulse wave sensor, an object (a user, or user's blood vessel in a narrow sense) is irradiated with light from the light emitting section, and reflective light or transmissive light is detected by the light receiving section. That is, in an operation of the pulse wave sensor, it is necessary to cause the light emitting section such as an LED to emit light, and thus, power consumption is relatively large.

Due to mounting of the pulse wave sensor, the activity state information detecting device is able to acquire pulse wave information and detect (calculate or operate) activity state information based on the pulse wave information, but power consumption of the device tends to increase. However, as understood from an example of a pedometer which is an example of a physical activity meter and is capable of being realized by a relatively simple configuration (in which the sensor is configured only by an acceleration sensor, for example), it is necessary that the physical activity meter be operated for a long period of time (for example, 24 hours).

In the case of the example of the pedometer, a user sets a target such as "10000 steps a day", and determines whether or not the target is achieved based on activity state information, that is, the number of steps detected by the pedometer. In such a situation, even though information of "6000 steps measured over 12 hours" is output, the user cannot appropriately determine whether or not the target is achieved, and thus, it cannot be said that the information is useful.

The activity state information detecting device may be assumed as a device to be worn by the user, and is commonly operated based on a battery or the like. That is, when the pulse wave sensor is mounted in the activity state information detecting device, it is important for the device to perform an efficient operation in consideration of power consumption. Otherwise, there is a possibility that the battery is dead, and as a result, it is difficult to output a measurement result over a long period of time desired by the user.

JP-A-2008-61663 discloses a device that includes a pulse wave sensor and reduces power consumption based on detected bio-information. However, JP-A-2008-61663 discloses a technique for controlling communication timing (transmission timing) based on a detection result of the bio-information, but does not consider specific contents of activity state information necessary in the device, the type of a sensor used for detection of the activity state information, or the like.

For example, in the activity state information detecting device capable of acquiring both the pulse wave information and the body motion information, as considered in the present embodiment, a situation where given activity state information can be obtained from pulse wave information or can be obtained from the body motion information may be considered. In such a situation, which sensor information is advantageously used in an operation of the activity state information may be changed according to a characteristic of each sensor or a user's state.

Based on these considerations, the present inventors propose a technique for switching a mode for obtaining activity state information depending on situations. Specifically, as shown in FIG. 1, an activity state information detecting device 100 according to the present embodiment includes a pulse wave measuring section 110 that measures the user's pulse wave information, a body motion measuring section 120 that measures the user's body motion information, and a processing section 130 that performs an operation process of the user's activity state information. Further, the processing section 130 performs a mode switching process between a first mode for performing the operation process of the activity state information based on the body motion information and a second mode for performing the operation process of the activity state information based on the pulse wave information.

Here, the activity state information may be a variety of information, and for example, may be information indicating user's calorie consumption for a measurement period. In this case, the processing section 130 calculates calorie consumption information as the activity state information based on the body motion information in the first mode, and calculates the calorie consumption information as the activity state information based on the pulse wave information in the second mode. A specific calculation method of the calorie consumption information in each mode will be described later.

The activity state information refers to information relating to user's activity specified based on bio-information measured by the device and setting information (for example, age, body height, or weight) which is user's individual information, in a broad sense. For example, the activity state information includes user's consumption calorie, movement distance, the number of steps, altitude change, speed, exercise intensity, a pulse rate threshold value used for sleep determination, sleeping hours, the quality of sleep, pulse zone setting, a physical strength level, estimated oxygen debt (EPOC), independent index values of an activity amount calculated based on these values, and the like.

With such a configuration, it is possible to appropriately switch the method (mode) for calculating the activity state information as necessary. Specifically, the processing section 130 may perform a process of setting the calculation mode of the activity state information to any one of the first mode for performing the operation process of the activity state information based on the body motion information and the second mode for performing the calculation process of the activity state information based on the pulse wave information. Thus, for example, it is possible to perform a control so that acquisition of the pulse wave information is not performed in the first mode. In this case, the pulse wave sensor may be turned off to skip the operation process of obtaining the pulse wave information, and thus, it is possible to perform an efficient operation in which power consumption is reduced. In this regard, the first and second modes do not represent only the operation modes of the activity state information in the processing section 130, but may also represent measurement modes of the activity state information detecting device 100. That is, as the mode setting is performed in the processing section 130, the operation process in the processing section 130 is determined, and also, an operation state (measurement state) of a given block such as the pulse wave measuring section 110 may be determined.

While the body motion information refers to information indicating user's body motion which is observable from an outer surface, the pulse wave information (for example, pulse rate) refers to information that reflects an internal activity (for example, a mental activity such as thinking) as well as an external activity such as a physical movement. Thus, even in the same activity state information, it may be considered that the accuracy becomes higher when the pulse wave information is used, compared with a case where the body motion information is used. However, as described above, the acquisition of the pulse wave information is disadvantageous due to large power consumption, compared with the acquisition of the body motion information. That is, it can be said that the technique of the present embodiment is a technique for selecting an appropriate mode according to situations in a trade-off relationship between accuracy and power consumption.

As described above, since the acquisition of the body motion information does not cause a particular problem in power consumption, the body motion information may be continuously acquired. Further, the acquisition of the pulse wave information may be performed with respect to only a situation where the importance of the acquisition of the pulse wave information is high. That is, in the present embodiment, for example, if the pulse wave information is acquired, the second mode may be selected, and if the pulse wave information is not acquired, the first mode may be selected. Further, when the acquisition of the pulse wave information is instructed through an operating section (not shown) of the activity state information detecting device 100, the second mode may be selected, and when the acquisition of the pulse wave information is not instructed, the first mode may be selected.

According to the technique of the present embodiment, it is possible to prevent stoppage of pulse measurement during measurement due to insufficient amount of remaining battery. Specifically, when the remaining battery is reduced, the device is operated so that the battery is saved, and is thus operated to measure the pulse wave information (pulse) only at a time when the measurement of the pulse wave information is desired.

Further, even when the amount of remaining battery is reduced such that the acquisition of pulse wave information (pulse measurement) cannot be set to ON, it is possible to operate the device in a mode (pulse wave OFF mode) where the acquisition of pulse wave information is set to OFF. That is, it is possible to continue the acquisition of the body motion information. Thus, it is possible to continuously measure information capable of being calculated based on only the body motion information, which is data that becomes a standard of a physical activity, such as the number of steps or calorie consumption.

For example, when there is no pulse wave OFF mode, if there is a day when the battery is dead, the measurement stoppage occurs, and thus, it is difficult to perform relative comparison with physical activities of other days. A case where the number of steps was 12000 yesterday and the number of steps is actually 15000 today but its count is 8000 steps since the battery becomes dead during measurement may occur. In this case, a user can view only the results of 12000 steps and 8000 steps, and determines that today's walk is short compared with yesterday in terms of only the numerical values, which does not reflect the actual situation. Further, even though the user can determine that the numerical value of 8000 steps is not reliable from a body sense, it is not easy to exactly estimate the number of steps.

In this regard, according to the technique of the present embodiment, since the pulse wave OFF mode is used as necessary, it is possible to suppress a possibility that necessary activity state information is omitted. Further, with respect to activity state information capable of being calculated from any one of the pulse wave information and the body motion information, although information to be used is changed due to mode switching, it is possible to continue the calculation in any mode. Thus, although the processing mode is switched for an efficient operation in the device, it is possible to continuously calculate calorie consumption while the user wears the device without causing the user to recognize the control.

Hereinafter, a specific configuration of the activity state information detecting device 100 according to the present embodiment will be described, and then, a specific method for switching the first and second modes will be described. Then, a calculation method of calorie consumption which is a specific example of the activity state information will be described, and finally, a specific example of a process in the second mode will be described with reference to FIG. 9A to FIG. 11B. In the second mode, since both of the body motion information and the pulse wave information can be acquired, a specific example of a process using the both modes will be described.

2. System Configuration Example

Figure 2:
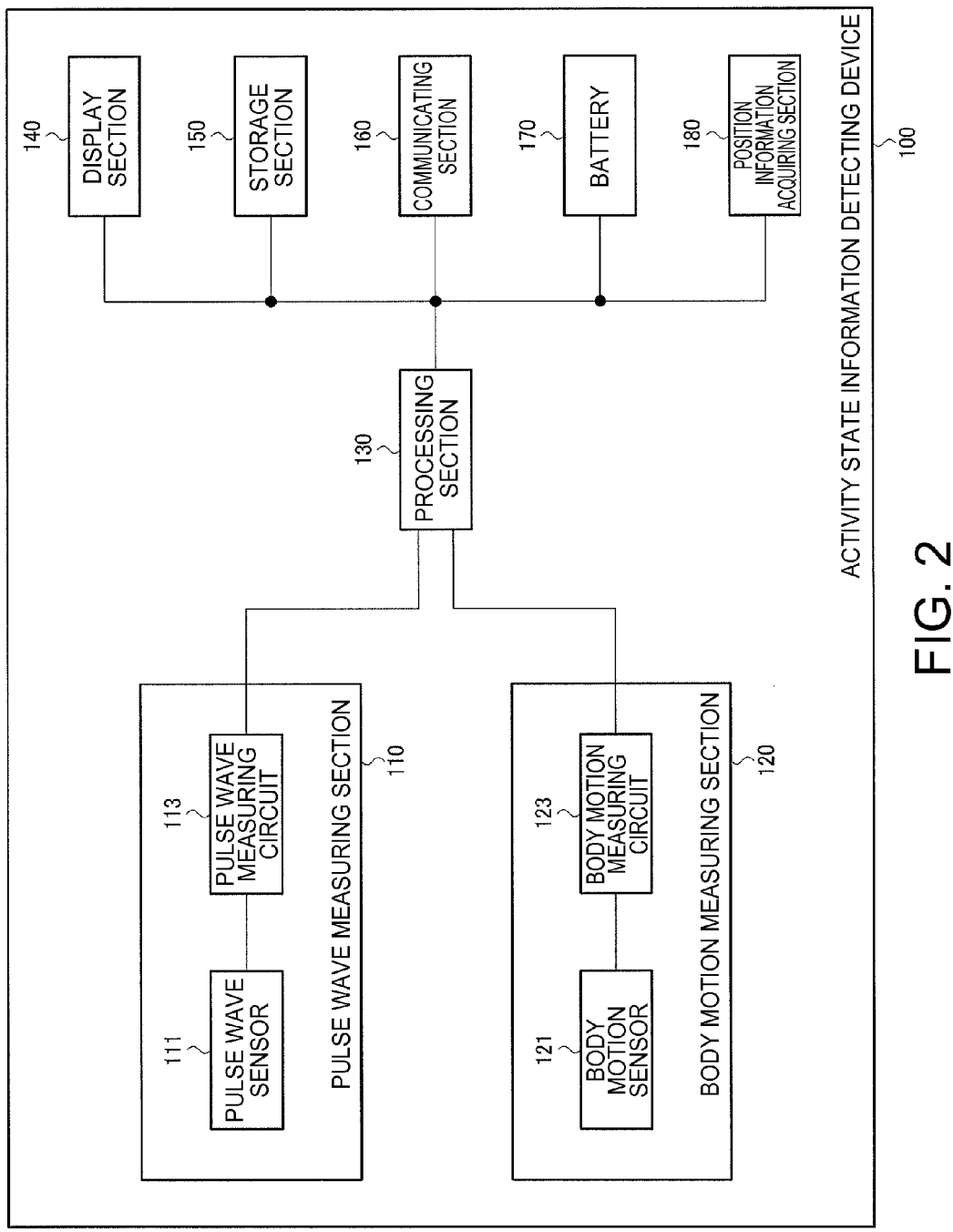
FIG. 2 is a diagram illustrating a detailed configuration example of an activity state information detecting device.

FIG. 2 shows a detailed configuration example of the activity state information detecting device 100 according to the present embodiment. As shown in FIG. 2, the activity state information detecting device 100 includes the pulse wave measuring section 110, the body motion measuring section 120, the processing section 130, a display section 140, a storage section 150, a communicating section 160, a battery (secondary battery) 170, and a position information acquiring section 180. Here, the activity state information detecting device 100 is not limited to the configuration shown in FIG. 2, and may have various modification examples such as a configuration in which a part of these components is not provided or changed or a configuration in which other components are added thereto.

The pulse wave measuring section 110 includes a pulse wave sensor 111 and a pulse wave measuring circuit (pulse wave detecting circuit) 113. The pulse wave sensor 111 is described as above, and the pulse wave sensor 111 may be a photoelectric sensor including a light emitting section and a light receiving section, for example. The pulse wave measuring circuit 113 is connected to the pulse wave sensor 111, and detects (acquires) pulse wave information based on sensor information from the pulse wave sensor 111.

The body motion measuring section 120 includes a body motion sensor 121 and a body motion measuring circuit (body motion detecting circuit) 123. The body motion sensor 121 is described as above, and the body motion sensor 121 may be an acceleration sensor, for example. The body motion measuring circuit 123 is connected to the body motion sensor 121, and detects (acquires) body motion information based on sensor information from the body motion sensor 121.

The processing section 130 performs various processes such as mode switching based on pulse wave information and body motion information. The function of the processing section 130 may be realized by hardware such as various processors (CPU or the like) or an ASIC (gate array or the like), a program, or the like. Details of a process in the processing section will be described later.

The display section 140 displays the detected activity state information. The display section 140 may be realized by a liquid crystal display, an organic EL display, or the like, for example. Here, the display of the activity state information may be performed by other devices (for example, a smart phone or a PC used by a wearer of the activity state information detecting device 100), and the activity state information detecting device 100 may have a configuration in which the display section 140 is not provided. In the activity state information detecting device 100 which will be described later with reference to FIG. 3A or the like, presentation of information to a user is performed by light emission of a light emitting section for interfacing through a light emitting window portion 32, and the display section 140 is not provided.

The storage section 150 is a work area of the processing section 130 or the like, and its function may be realized by a memory such as a RAM, a hard disk drive (HDD), or the like. The storage section 150 may store pulse wave information and body motion information, or may store detected activity state information. Further, the storage section 150 may store schedule information or the like which will be described later with reference to FIGS. 6A and 6B.

The communicating section 160 performs communication with other devices. The communicating section 160 may transmit the activity state information calculated by the processing section 130, or may receive information (for example, schedule information or the like) used in the mode switching process from other devices.

Communication of the communicating section 160 may be performed through a network NE. The network NE may be realized by a wide area network (WAN), a local area network (LAN), or the like, in a wired manner or a wireless manner. For example, when a device which is a communication target is a server system provided at a position physically remote from the activity state information detecting device 100, the network NE may be the Internet or the like. Further, when the device which is the communication target is a smart phone used by the same user as that of the activity state information detecting device 100, the network NE may be a short-range wireless communication network or the like.

The battery 170 supplies power to the respective sections of the activity state information detecting device 100. The battery 170 may be realized by a secondary battery such as a lithium ion battery or the like, for example.

The position information acquiring section 180 acquires position information indicating a user's position (current position in a narrow sense). The position information acquiring section 180 may include a global positioning system (GPS) antenna or the like, and may acquire position information using a GPS. Alternatively, the position information may be information acquired from a mobile phone base station or the like. A process using the position information will be described later.

Figure 3A:
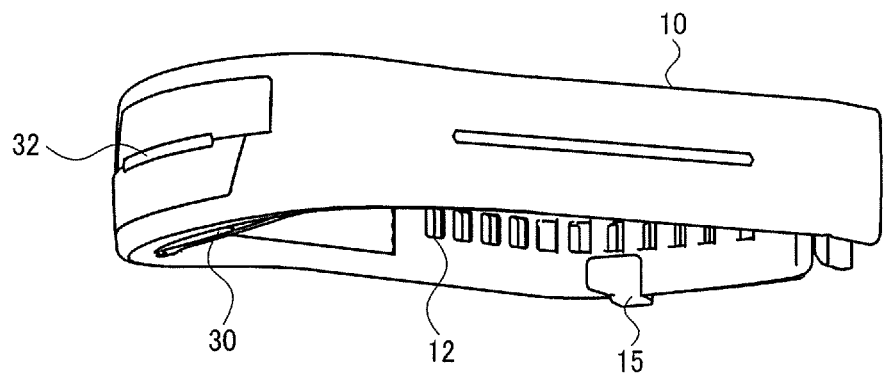
FIGS. 3A and 3B are diagrams illustrating an appearance of an activity state information detecting device.
Figure 3B:
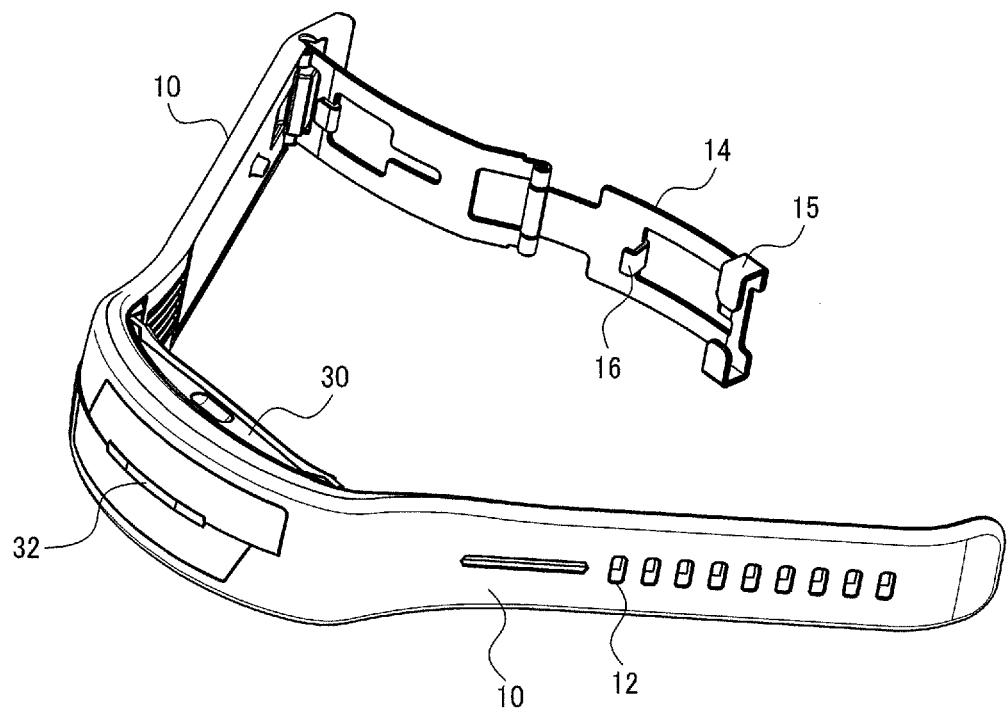
Figure 4:
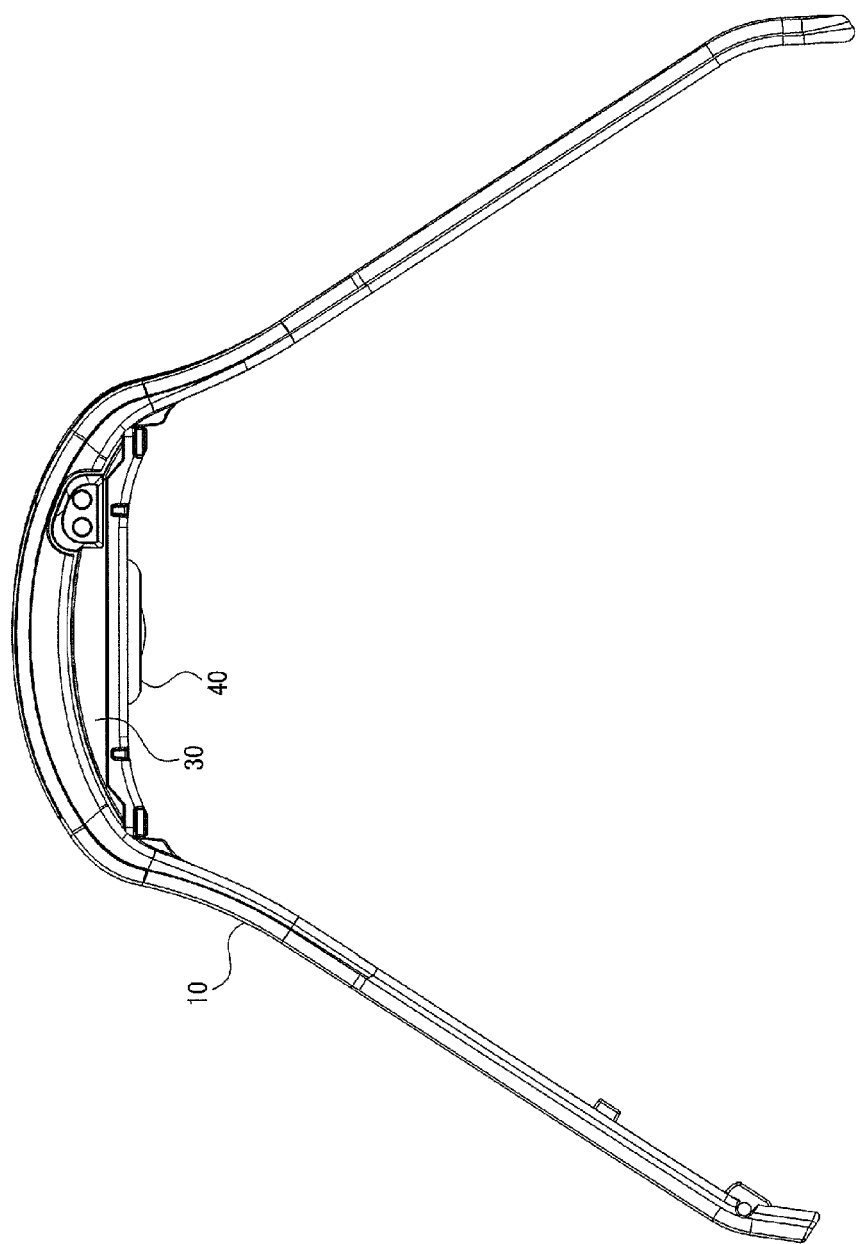
FIG. 4 is a diagram illustrating an appearance of an activity state information detecting device.

FIG. 3A to FIG. 4 show an example of an appearance of the activity state information detecting device 100 according to the present embodiment. The activity state information detecting device 100 of the present embodiment includes a band portion 10, a case portion 30, and a sensor portion 40. The case portion 30 is attached to the band portion 10. The sensor portion 40 is provided in the case portion 30.

Here, the sensor portion 40 has a configuration in which light can be output to the outside through a light transmitting member and light can be received from the outside, and in a narrow sense, the pulse wave sensor 111 may be provided as the sensor portion 40. The activity state information detecting device 100 according to the present embodiment includes the body motion sensor 121 as described above, but the body motion sensor 121 may be included in the sensor portion 40 shown in FIG. 4, or may be provided in another portion of the activity state information detecting device 100.

The band portion 10 is wound on a user's wrist to mount the activity state information detecting device 100. The band portion 10 includes band holes 12 and a buckle portion 14. The buckle portion 14 includes a band inserting portion 15 and a protruding portion 16. As the user inserts one end of the band portion 10 into the band inserting portion 15 of the buckle portion 14 and inserts the protruding portion 16 of the buckle portion 14 into a band hole 12 of the band portion 10, the activity state information detecting device 100 is mounted on the wrist.

The case portion 30 corresponds to a main body portion of the activity state information detecting device 100. Various components of the activity state information detecting device 100 such as the sensor portion 40 and a circuit board (not shown) are provided inside the case portion 30. That is, the case portion 30 serves as a housing that accommodates the components.

The light emitting window portion 32 is provided in the case portion 30. The light emitting window portion 32 is formed of a light transmitting member. Further, a light emitting portion which is an interface mounted on a flexible board is provided in the case portion 30, and light from the light emitting section is output to the outside of the case portion 30 through the light emitting window portion 32.

The activity state information detecting device 100 is mounted on the user's wrist as shown in FIG. 5A, for example, and measurement of pulse wave information (bio-information in a broad sense) or body motion information is performed in the mounted state.

Further, the activity state information detecting device 100 according to the present embodiment is not limited to a wearable device to be mounted to a user, and may be a server system. In this case, the pulse wave measuring section (pulse wave information acquiring section) 110 acquires pulse wave information from a wearable device with the pulse wave sensor 111, and the body motion measuring section (body motion information acquiring section) 120 acquires body motion information from a wearable device with the body motion sensor 121. Further, considering that the technique of the present embodiment is used to efficiently operate a device with a restriction in a battery or the like, the processing section 130 may perform mode switching, and also, may give an instruction for switching an operation state (ON/OFF) of the pulse wave sensor 111 to a wearable device. In this example, the wearable device or the like may perform acquisition of the pulse wave information and the body motion information, and an actual calculation may be executed by the activity state information detecting device 100 which is a server system.

It is necessary that a wearable device to be worn by a user be small and lightweight, which causes various restrictions in the processing performance of a processing section in the device or data storage capacity. On the other hand, since a server system has relatively small restrictions on resources, calculation of activity state information or a process relating to mode switching may be performed at high speed, or a large amount of data (pulse wave information, body motion information or activity state information) may be retained. Further, by applying appropriate feedback to a wearable device from the activity state information detecting device 100 which is the server system according to the mode switching result, the wearable device may be efficiently operated.

Such an example is shown in FIG. 5A, in which the activity state information detecting device 100 which is the server system is connected to a wearable device 200 through the network NE, and acquires pulse wave information and body motion information from the wearable device 200.

Since it is sufficient if the activity state information detecting device 100 can acquire the pulse wave information and the body motion information collected by the wearable device 200, a case where the activity state information detecting device 100 is directly connected to the wearable device 200 is not essential. For example, as shown in FIG. 5B, a configuration in which the wearable device 200 is connected to another processing device 400 and the activity state information detecting device 100 is connected to the processing device 400 through the network NE may be used. In this case, a portable terminal such as a smart phone used by the user who wears the wearable device 200 may be used as the processing device 400. Further, the connection between the wearable device 200 and the processing device 400 may be performed through a network with the same configuration as the network NE, or a short-range wireless communication network or the like.

Further, the activity state information detecting device 100 according to the present embodiment may be realized by a processing device (portable terminal in a narrow sense) such as a smart phone, instead of the server system. A configuration example in this case is shown in FIG. 5C. A portable terminal such as a smart phone has many restrictions on its processing performance, storage area, and battery capacity compared with the server system, but sufficient processing performance or the like may be secured in view of recent performance improvement. Accordingly, as long as a request for the processing performance improvement is satisfied, as shown in FIG. 5C, the smart phone or the like may be used as the activity state information detecting device 100 according to the present embodiment.

In the above description, an example in which the activity state information detecting device 100 is realized by one device among the server system, the processing device 400, and the wearable device 200 is shown, but the invention is not limited thereto. For example, the acquisition of the pulse wave information and the body motion information, the accumulation process of the acquired information, the mode switching process, and the switching instruction of the operation state of the pulse wave sensor 111 may be realized by distributed processes of plural devices. Specifically, the activity state information detecting device 100 may be realized by at least two or more devices among the server system, the processing device 400, and the wearable device 200. Further, the processes according to the present embodiment may be performed by other devices, or the activity state information detecting device 100 according to the present embodiment may be realized by various devices (or a combination of devices).

In other words, the technique of the present embodiment may be applied to an active state information detecting system including the pulse wave measuring section 110, the body motion measuring section 120, and the processing section 130, and the activity state information detecting system may be configured by one or plural devices.

3. Mode Switching Method

Next, a specific determination method for switching the first mode and the second mode will be described. Specifically, determination based on the amount of remaining battery, particularly, behavior determination based on body motion information, determination based on schedule information or the like, and determination based on position information will be individually described, and then, combinations thereof will be described.

3.1 Determination Based on Amount of Remaining Battery

The processing section 130 may perform the mode switching process based on the amount of remaining battery. As described above, in the present embodiment, a situation where pulse wave information cannot be measured at a time when measurement is important, or a situation where activity state information such as the number of steps cannot be acquired over a necessary period of time (for example, continuously for 24 hours) due to a dead battery is problematic. That is, whether the amount of remaining battery is sufficient or not is an important determination element in the mode switching.

Specifically, when the amount of remaining battery is equal to or greater than a predetermined amount of remaining battery, the processing section 130 sets the second mode, and when the amount of remaining battery is smaller than the predetermined amount of remaining battery, the processing section 130 may set the first mode or the second mode.

As described above, when obtaining predetermined activity state information, it is generally considered that it is possible to increase the accuracy when using the pulse wave information, compared with a case where the body motion information is used. Accordingly, when the amount of remaining battery is sufficient, the pulse wave information may be positively used in the process, and thus, the second mode is selected as the mode.

On the other hand, when the amount of remaining battery is small, it is preferable to suppress the possibility of a dead battery, if possible, and thus, the setting of the first mode should be considered. Since the acquisition of the body motion information causes less power consumption compared with the acquisition of the pulse wave information, there is no problem even though the body motion information is operated with high frequency (continuously in a narrow sense). Thus, during the operation of the activity state information detecting device 100, it is considered that the calculation of the activity state information based on the first mode is possible.

However, depending on the circumstances, a case where it is preferable to acquire the pulse wave information may be considered. Specifically, a situation which is determined as an exercise state in behavior determination (which will be described later) is an example of such a case. In this case, since if the pulse wave information cannot be acquired, the disadvantage may be significant, and even though the amount of remaining battery is small, the pulse wave information may be acquired. In such a case, since it is not reasonable to calculate the activity state information in the first mode (using the body motion information) while acquiring the pulse wave information, the second mode may be set. That is, in this example, when the amount of remaining battery is small, whether to set the first mode or the second mode is determined in consideration of other determination results.

The determination method based on the amount of remaining battery is not limited to the above description. For example, when the amount of remaining battery is sufficient (equal to or greater than the predetermined amount of remaining battery), the first mode may be set. Even though the amount of remaining battery is sufficient at a predetermined timing, there is a possibility that the battery is dead in consideration of a subsequent continuous operation time. For example, at a timing immediately after the activity state information detecting device 100 is separated from a charger to start its use (measurement), the amount of remaining battery is close to 100%, which is equal to or greater than the predetermined amount of remaining battery. However, after the timing, since it is necessary that the activity state information detecting device 100 is continuously operated for a long period of time (for example, for 24 hours), a large amount of remaining battery at a current timing does not lead to determination of a low possibility of a dead battery. In such a case, although the amount of remaining battery is sufficient, a process of setting the first mode may be performed for the future.

In this case, a determination result regarding whether the amount of remaining battery is equal to or greater than a predetermined threshold value or smaller than the predetermined threshold value may affect the possibility of the selection of each of the first and second modes. For example, when the amount of remaining battery is equal to or greater than the predetermined threshold value, the possibility that the second mode is set is high, and the possibility that the first mode is set is low, compared with a case where the amount of remaining battery is smaller than the predetermined threshold value. With such a configuration, when there is a margin in the amount of remaining battery, it is possible to increase the possibility that the pulse wave information is used (to preferentially consider the pulse wave information) while maintaining the possibility that both modes are set regardless of the amount of remaining battery.

Further, in the above description, an example in which one predetermined threshold value is used, but the invention is not limited thereto. For example, two or more threshold values of the amount of remaining battery may be used, so that the amount of remaining battery may be divided into three or more states. In this case, similarly, as the amount of remaining battery is large, the possibility that the second mode is set is high (a process of setting only the second mode may be performed), and as the amount of remaining battery is small, the possibility that the first mode is set is high (a process of setting only the first mode may be performed).

Behavior Determination

Further, when it is determined that a user is in an exercise state or a sleep state based on body motion information, the processing section 130 may set the second mode. Here, the exercise state indicates a state where the user does exercise (running, walking, sports, or the like), and specifically corresponds to a state where the size of a body motion represented by the body motion information is large. In addition, the sleep state represents a "sleep" state which is generally used when the level of consciousness (and response to external stimuli) in a resting state is low.

In the exercise state, it is useful to acquire information such as a pulse rate. Since the pulse rate is not information simply indicating the size of a body motion but is information fundamentally reflecting the degree to which the user is active, the pulse rate appropriately represents the degree of load due to exercise. Thus, by acquiring pulse wave information about the pulse rate or the like, it is possible to determine whether a current exercise is an appropriate load for a target user, and thus, it is also possible to determine whether the load is appropriate for fat burning. Further, since excessive load exercise is not preferable in view of user's health, it is possible to suppress such exercise.

That is, since it is important to acquire the pulse wave information in the exercise state, with respect to other activity state information, similarly, it is preferable that information capable of being obtained from the pulse wave information is calculated using the pulse wave information. In other words, when it is determined that the user is in the exercise state, the second mode is set.

On the other hand, in the sleep state, the depth of sleep may be determined. A deeper sleep (for example, non-REM sleep) is a state where a user's activity is suppressed compared with a shallower sleep (for example, REM sleep), and in this state, the brain and the body are in a resting state. That is, the depth of sleep may be used as information indicating the quality of sleep. Particularly, since simple sleeping hours may be recognized by the user to some extent but it is considerably difficult for the user to recognize the depth of sleep, presentation of the information relating to the depth of sleep to the user is significant. Further, since it is difficult to calculate the information relating to the depth of sleep from the body motion information with high accuracy, it is preferable that the information relating to the depth of sleep is calculated using the pulse wave information. The depth of sleep may be calculated from a process of comparing a pulse rate with a predetermined pulse rate threshold value, or may be calculated by autonomic nerve activity information (widely known LF and HF) obtained from a pulse period or the like.

That is, since it is important to obtain the pulse wave information even in the sleep state, when it is determined that the user is in the sleep state, the second mode may be set.

In determination of the exercise state and determination of the sleep state, the body motion information may be used. In a narrow sense, determination using an acceleration value may be performed. Specifically, since the body motion is large in the exercise state, when the acceleration value is equal to or greater than a predetermined exercise acceleration threshold value, it is determined that the body motion is in the exercise state. Similarly, since the body motion in the sleep state is considerably small, when the acceleration value is equal to or smaller than a predetermined sleep acceleration threshold value, it may be determined that the body motion is in the sleep state. Various techniques for determining the exercise state from the body motion information are known. For example, since exercise such as running or walking has periodicity, a signal indicating a temporal change of an acceleration value has also periodicity. The determination of the exercise state may use such a technique for determining the presence or absence of the periodicity.

Further, when it is determined that the user is in a resting state based on the body motion information, the processing section 130 may set the first mode. The resting state refers to a state where the user is in a state of being awake and the body motion is small in size compared with the exercise state. When the user is in the resting state, since the pulse rate may be considered as a relatively small stable value, even though the acquisition of the pulse wave information is not performed, there is no particular problem.

At a time when a rapid change of a pulse rate is detected even in the resting state, it may be determined that a certain abnormality occurs in the user, and thus, the acquisition of the pulse wave information in the resting state may be significant. However, in the present embodiment, in order to realize an efficient operation of the activity state information detecting device 100, the acquisition of the pulse wave information in the resting state is handled to have a low priority compared with the exercise state or the sleep state. That is, when it is determined that the body motion is in the resting state, the first mode is set, and the acquisition of the pulse wave information may not be performed.

The determination of the resting state based on the body motion information may be performed by threshold value determination as described above. For example, the sleep acceleration threshold value and the exercise acceleration threshold value are set so that the sleep acceleration threshold value is smaller than the exercise acceleration threshold value, and when the acceleration value is larger than the sleep acceleration threshold value and is smaller than the exercise acceleration threshold value, it may be determined that the body motion is in the resting state.

Here, since the body motion may be considerably small in size in the resting state, it is not easy to determine whether the body motion is in the sleep state or in the resting state with high accuracy from only the body motion information. For example, in a state where the user lies down on a bed in a state of being awake, and in a state where the user lies down on the bed in the sleep state, acceleration values may be small to the same degree, and thus, with the determination based on the comparison of the acceleration value with the sleep acceleration threshold value, it may be difficult to appropriately distinguish the two states.

During operation in the first mode, since the acquisition of the pulse wave information may not be performed, it is assumed that the determination regarding whether the body motion is in the sleep state or in the resting state is also performed using the body motion information. If information about another sensor (here, sensor other than the pulse wave sensor 111) provided in the activity state information detecting device 100 or information from another device that communicates with the communicating section 160 is useful for the distinction between the sleep state and the resting state, the information may be used.

On the other hand, during operation in the second mode, since the acquisition of the pulse wave information is performed, the determination regarding whether the body motion is in the sleep state or in the resting state may be performed using both of the body motion information and the pulse wave information. Although details thereof will be described later, it is possible to determine the sleep state with high accuracy by using both of the body motion information and the pulse wave information (particularly, change information on both the information).

In view of the above description, the necessity for performing the distinction between the resting state and the sleep state in the first mode with high accuracy is not so high. The reason is as follows. That is, even though the resting state is erroneously determined as the sleep state in the first mode, since the mode transitions to the second mode according to the determination result, the determination may be performed with high accuracy based on both of the body motion information and the pulse wave information. That is, even though the mode transitions to the second mode according to the erroneous determination, the mode may return to the first mode at a timing of the next mode switching process, and thus, it may be considered that power loss is not severe.

Here, when it is erroneously determined that the body motion is in the resting state even though the body motion is actually in the sleep state, the first mode is continued, and thus, it is not possible to perform the determination with high accuracy using the pulse wave information. As a result, the first mode is continuously set even though the second mode is appropriate, which is not preferable.

Accordingly, in the present embodiment, in the determination using the body motion information, it may be easily determined that the body motion is in the sleep state. Then, since a probability that the mode transitions to the second mode increases, it is possible to perform the determination regarding whether the body motion is in the sleep state or in the resting state with high accuracy. For example, in the determination using the body motion information, it may be determined that the body motion is in any one of the exercise state or the sleep state and is not in the resting state. Here, if a period when the operation is performed in the second mode is long, power consumption increases, and thus, the advantages due to the technique according to the present embodiment decrease. Thus, the determination technique using the body motion information may be changed in consideration of the determination accuracy and power consumption, and thus, various modification examples may be used.

Further, when it is determined that the body motion is in the sleep state, a configuration in which the pulse wave information is intermittently acquired in the first mode may be used. For example, in the second mode, the pulse wave information may be continuously acquired to calculate the pulse rate every second or every 4 seconds, and in the first mode, the pulse wave information may be acquired for only 1 minute in a 10 minute period to calculate the pulse rate at predetermined time intervals or only once with respect to only the information acquired for 1 minute.

Further, the pulse wave information may be intermittently acquired in the second mode as described above, without acquiring the pulse wave information in the first mode. With such a configuration, it is possible to reduce the frequency of pulse rate measurement during sleep when a variation is relatively small, and thus, it is possible to reduce power consumption. In addition, with such a configuration, it is possible to perform physical activity measurement in serious consideration of the acquisition of pulse wave information (or a continuation time thereof) during daytime activities compared with sleeping.

3.3 Determination Based on Schedule Information and Timing Information

Further, the processing section 130 may perform the mode switching process based on at least one of schedule information and timing information.

Here, the schedule information refers to information indicating association of a predetermined time zone and priority (ON/OFF in a narrow sense) of pulse wave measurement in the time zone. An example of the schedule information is shown in FIGS. 6A and 6B. FIGS. 6A and 6B are data tables in which a schedule for setting measurement of pulse wave information to ON is defined, which may be configured by a database, for example. The schedule may be defined by date and time as shown in FIG. 6A, may be defined by a day of the week as shown in FIG. 6B, or may be defined in other forms.

In the example shown in FIG. 6A, at 6:00 to 8:00 on Jul. 19, 2014, activity state information is obtained by setting pulse wave measurement to ON, that is, in the second mode. Similarly, at 18:00 to 19:00 on Jul. 23, 2014, and at 6:00 to 8:00 on Jul. 26, 2014, the second mode is set.

In the example shown in FIG. 6B, since the second mode is set at 6:00 to 8:00 on Sunday, in a state where this schedule information is set, the second mode is set at 6:00 to 8:00 every Sunday. Further, as shown in schedule information called WEEK003 in FIG. 6B, the day of the week may not be set. For example, in a state where this schedule information is set, the second mode may be set at 6:00 to 8:00 every day.

When the schedule information is used, it is necessary that the activity state information detecting device 100 acquires information about a current timing (timing information) and performs a process of comparing the current timing with a timing (time) regulated in the schedule information. For example, the activity state information detecting device 100 may include a timer (not shown in FIG. 2), and may acquire timing information by the timer. Alternatively, the activity state information detecting device 100 may acquire timing information from another device through the communicating section 160.

Further, here, a specific example of the schedule information for setting the pulse wave measurement to ON is shown, but schedule information for setting the pulse wave measurement to OFF may be provided. When the ON schedule and the OFF schedule are temporarily overlapped, it may be considered that a setting error occurs. Thus, the activity state information detecting device 100 may notify the user of the error, or may prioritize any one of the schedules.

Each type of schedule information may be input by a user interface operation. Here, the user interface operation may refer to a user operation of an operating section (not shown in FIG. 2 or the like, but for example, a button or the like) of the activity state information detecting section 100, or a user operation of an interface of another device that communicates with the activity state information detecting device 100.

Further, the schedule information is not limited to the user's setting. For example, when history information on a continuation time of the above-described behavior determination process or each behavior is accumulated, and when there are plural similar behaviors (exercises), software may be mounted so that schedule information is registered. For example, during the time of 18:00 to 19:00 on Friday, when it is understood that the exercise state is detected with high frequency from predetermined user's history information, schedule information as shown in WEEK002 in FIG. 6B may be automatically generated.

In addition, in the above description, an example in which in a time zone regulated in the schedule information, the pulse wave measurement is necessarily determined to be set to ON or OFF is shown, but the invention is not limited thereto. For example, as described later, another determination technique such as the amount of remaining battery or behavior determination may be combined. In such a case, the schedule information and the timing information do not fix ON or OFF (the first mode or the second mode), and may be used as information for determining which one of ON and OFF is preferentially selected.

In the above description, an example in which both of the schedule information and the timing information are used is shown, but the invention is not limited thereto. The mode switching process may be performed using only the timing information. Specifically, since most users are in the sleep state in a time zone of midnight, a process of setting the second mode, or increasing the priority of the second mode may be performed. Here, since it is not effective to use the process based on the timing information for only a behavior tendency of an individual user, the process based on the timing information may be used for determination with high versatility as in the above-described example relating to the sleep state.

Further, an example in which the schedule information is used as the information indicating the association of the predetermined time zone and the priority (ON/OFF in a narrow sense) of the pulse wave measurement in the time zone is shown, but the information associated with the time zone is not limited to information directly indicating ON or OFF of the pulse wave measurement. For example, as described above, it is known that the importance of the pulse wave measurement is high in the exercise state or the sleep state. That is, the information associated with the predetermined time zone in the schedule information may be information indicating the user's behavior state, for example.

For example, a column indicating "behavior state" may be added to the schedule table shown in FIG. 6B, and values of "exercise state" or "sleep state" may be stored in the column. In the exercise state or the sleep state, since it is sufficient if the pulse wave measurement is set to ON, that is, the second mode is set, schedule information indicating that "behavior information" is "exercise state" or "sleep state" may be treated as schedule information for setting the pulse wave measurement to ON.

Specifically, when it is determined that the user is in the exercise state or the sleep state based on at least one of the schedule information and the timing information, the processing section 130 may set the second mode. Thus, the user's behavior determination may be performed from the schedule information, and the mode switching may be performed according to a behavior corresponding to the determination result.

The schedule information is not only used by one user, but also, may be shared or exchanged by a user account of another person, for example. For example, when plural users belong to the same sport club, a possibility that the plural users do exercise at the same time is high, and thus, schedule information indicating an exercise time zone may be shared. Specifically, when a representative or the like of the circle sets schedule information using his/her own user account, an embodiment in which the schedule information is distributed to other user accounts that belong to the circle may be considered, for example.

Determination Based on Position Information

Further, the activity state information detecting device 100 according to the present embodiment may include the position information acquiring section 180 that acquires position information of a user, as shown in FIG. 2. Further, the processing section 130 performs the mode switching process based on the position information.

The position information according to the present embodiment may include both of a current position of the user and a reference position which becomes a reference for the mode switching process. Here, the reference position refers to a place for which it is determined that it is preferable to perform a predetermined mode switching when the user is at the place or is close to the place.

For example, the reference position may be a position (place) recognized as a running course, or a position used as a course at a marathon race or the like. When the user is at such a position, since it is estimated that the user is in an exercise state of running, it may be determined that it is sufficient if the pulse wave measurement is set to ON, that is, if the second mode is set, as described above. In other words, when it is determined that the user is in the exercise state based on the position information, the processing section 130 may set the second mode.

Each type of position information may be data acquired from a GPS or a mobile phone base station, or data on latitude and longitude calculated based on the data. Further, the position information is not limited to information indicating one point, and may be data indicating a certain range indicating a position. In addition, the position information may have a list data structure in which plural positions are connected by points. In the list data structure, path information data indicating a passage path may be used. Information on the reference position in the position information may be stored in the storage section 150 in advance, similar to the schedule information described above using FIG. 6A or the like.

In the present embodiment, the mode switching process may be performed through a process of comparing the current position with the reference position. Specifically, when it is detected that the user (current position) is close to the above-described position information (reference position) within a predetermined distance range, the pulse measurement is started, and the second mode is set.

Further, when the reference position is provided in a format of the path information data, it may be determined whether the user travels on a vector of the path, in addition to determination regarding whether the current position is close to the path information within the predetermined distance range. For example, a situation in which a road extending in an east-west direction is set as a running course at the reference position and the user moves on a road extending in a south-north direction that crosses the road may be considered. In this case, in a state where the user is present at an intersection of two roads, it may be determined that the current position is close to the reference position (path information) within the predetermined distance range. However, in reality, since the user only moves on a path different from the running course, it is not appropriate to determine that the user is doing exercise from the determination result. That is, whether the movement direction of the user follows the path direction is also an important determination element with respect to the path information, and in this example, determination regarding whether or not the user moves in the east-west direction may be determined in association with the distance determination. The movement direction of the user may be determined using a history of information on the current position.

Further, in the above description, an example in which, when the current position is close to the predetermined position (reference position), the pulse wave measurement is set to ON and the second mode is set is shown, but the invention is not limited thereto. For example, when the current position is close to the predetermined position, position information (path information) may be designated so that the pulse measurement is set to OFF and the first mode is set.

3.5 Combination Example of Plural Determinations

In the above description, the determination based on the amount of remaining battery, particularly, the behavior determination based on the body motion information, the determination based on the schedule information or the like, and the determination based on the position information are individually described, but in the present embodiment, these determinations may be combined.

Figure 7:
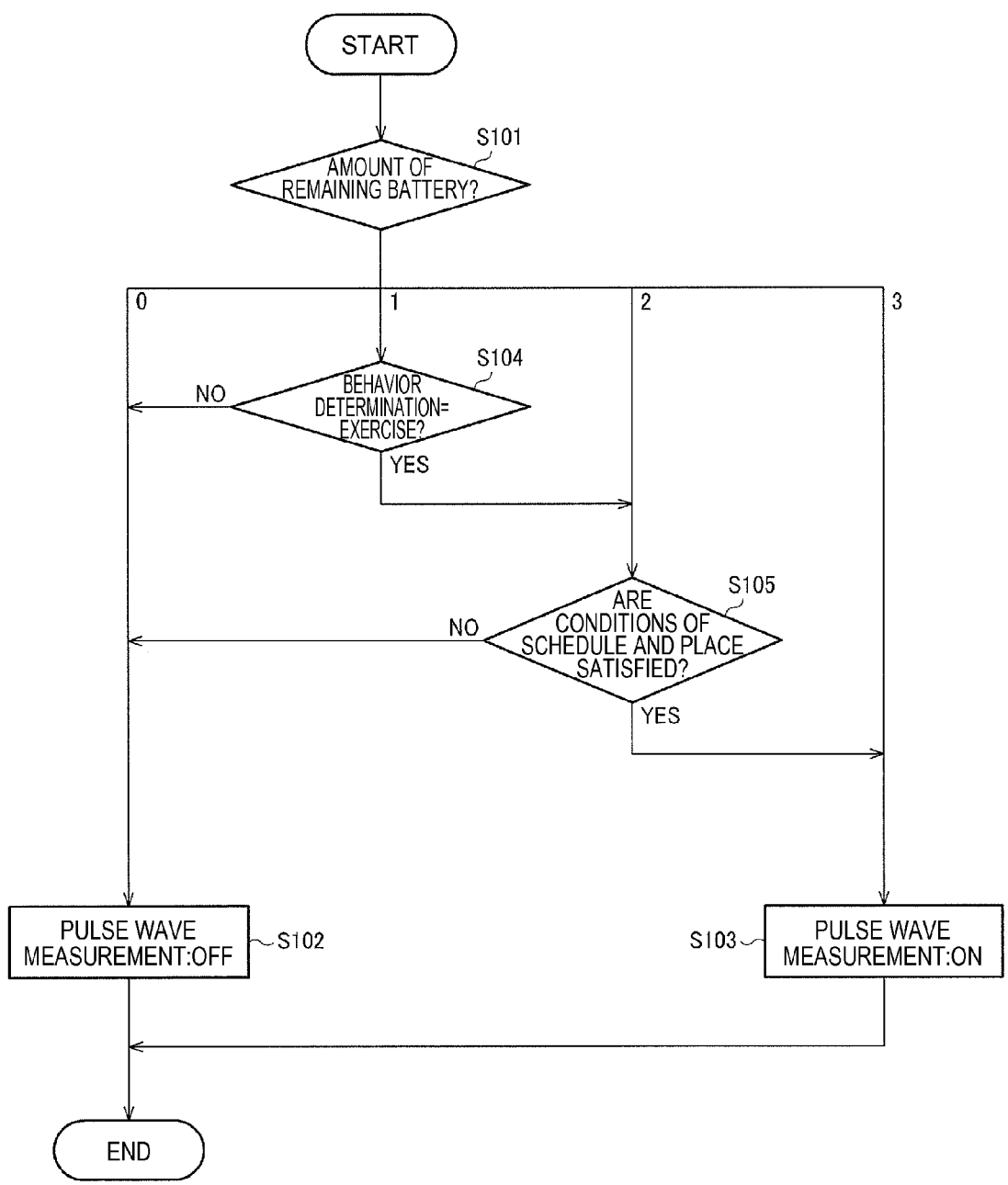
FIG. 7 is a flowchart illustrating a mode switching process according to an embodiment of the invention.

FIG. 7 is a flowchart illustrating an example of a process in such a combination. If the process is started, first, determination relating to the remaining battery is performed (S101). In the example shown in FIG. 7, the determination of the remaining battery is performed with respect to four stages of 0 to 3, in which the remaining battery is the maximum in stage 3, and is the minimum in stage 0.

When it is determined in S101 that the amount of remaining battery is stage 0, pulse wave measurement is set to OFF without performing another determination, and the activity state information is obtained by the first mode (S102). That is, in the example shown in FIG. 7, at a time when the amount of remaining battery has no margin, the power saving is preferentially considered without referring to a behavior state, a schedule, or the like.

On the other hand, when it is determined in S101 that the amount of remaining battery is stage 3, the pulse wave measurement is set to ON without performing another determination, and the activity state information is obtained by the second mode (S103). That is, in the example shown in FIG. 7, at a time when the amount of remaining battery has a considerably sufficient margin, the acquisition of pulse wave information is preferentially considered without referring to a behavior state, a schedule, or the like.

In the example shown in FIG. 7, even though the necessity of acquisition of pulse wave information is high, if the amount of remaining battery is considerably small, the pulse wave measurement is set to OFF, and even though the necessity of acquisition of pulse wave information is low, if the amount of remaining battery is considerably large, the pulse wave measurement is set to ON, which is an allowable example.

Further, when it is determined in S101 that the amount of remaining battery is stage 1, determination regarding whether the user is in an exercise state by the behavior determination (S104). When the determination result is negative in S104, the procedure proceeds to S102 to set the pulse wave measurement to OFF. In this case, since the amount of remaining battery has a relatively small margin and the user is not in the exercise state, it is determined that the necessity for pulse wave measurement is not high, and thus, the pulse wave measurement may be set to OFF.

On the other hand, when the determination result is affirmative in S104, since the user is in the exercise state, it is determined that the necessity for pulse wave measurement is high. Then, the procedure does not immediately proceed to S103, and determination based on schedule information and position information is performed (S105). The determination in S105 may be affirmative when both conditions of the schedule information and the position information are satisfied, or may be affirmative when at least one of the schedule information and the position information is satisfied. Here, in S105, the schedule information and the position information (reference information) for setting the pulse wave measurement to ON are considered. As described above, schedule information and position information (reference position) for setting the pulse wave measurement to OFF may be considered, and in this case, when any condition is not satisfied, it is determined that the result in S105 is affirmative.

When the determination result in S105 is affirmative, since it is determined that the necessity for pulse wave measurement is high from the determination of the schedule information or the position information, the procedure proceeds to S103 to set the pulse wave measurement to ON. On the other hand, when the determination result in S105 is negative, since it is determined that the necessity for pulse wave measurement is low, the procedure proceeds to S102 to set the pulse wave measurement to OFF.

That is, when it is determined that the amount of remaining battery is stage 1, and when the determination result is affirmative in S104 and the determination result is affirmative in S105, the procedure proceeds to S103 to set the pulse wave measurement to ON, and in other cases, the procedure proceeds to S102 to set the pulse wave measurement to OFF. On the other hand, when it is determined in S101 that the amount of remaining battery is stage 2, the procedure proceeds to S105. Then, when the determination result in S105 is affirmative in S101, the procedure proceeds to S103, and when the determination result in S105 is negative, the procedure proceeds to S102.

When the amount of remaining battery is stage 1 or stage 2 which is a medium level, the mode is changed according to conditions other than the amount of remaining battery. Here, when the amount of remaining battery is stage 1 where the amount of remaining battery is relatively low, only if the determination results in both of S104 and S105 are affirmative, the pulse wave measurement is set to ON, but when the amount of remaining battery is stage 2 where the amount of remaining battery is relatively high, if the determination result in S105 is affirmative, the pulse wave measurement is set to ON, and the behavior determination result does not matter. The reason is as follows. That is, when the amount of remaining battery has a relative large margin, even though the pulse wave measurement is easily set to ON, that is, even though the conditions for setting the pulse wave measurement to ON are loosened, a possibility that the battery is dead is low, but when the amount of remaining battery has a relatively small margin, if the conditions for setting the pulse wave measurement to ON are not strict so that the pulse wave measurement is not easily set to ON, a possibility that the battery is dead is high.

The process described in the flowchart of FIG. 7 is an example of the combinations, and other modification examples may be used. For example, in FIG. 7, only the combination of the amount of remaining battery and the exercise state determination is described, but a combination with other behavior determinations may be used.

For example, when the amount of remaining battery is smaller than a predetermined amount of remaining battery, and when it is determined that the user is in the exercise state or the sleep state based on the body motion information, the processing section 130 may set the second mode. Further, when the amount of remaining battery is smaller than the predetermined amount of remaining battery, and when it is determined that the user is in the resting state based on the body motion information, the processing section 130 may set the first mode.

With such a configuration, it is possible to set the mode by combining the determination results of the sleep state, the resting state or the like, as well as the exercise state, with the determination result of the amount of remaining battery.

Further, as described above in S105, the schedule information and the position information (path information) may be independently used as a trigger for the start and termination of the pulse measurement. Further, the pulse measurement may be started and terminated only when both the conditions are satisfied. The schedule, position and path information may be collectively managed.

In addition, various combinations may be used as the conditions for setting the pulse wave measurement to OFF and setting the first mode. For example, when the schedule information condition is not satisfied (a current timing is out of a schedule range where the pulse wave measurement is set to ON), and when the behavior determination does not indicate the exercise state, the pulse wave measurement may be set to OFF. Alternatively, when the position information condition is not satisfied (a current position is out of a range of position information or path information), and when the behavior determination does not indicate the exercise state, the pulse wave measurement may be set to OFF.

In this way, by adding "when the behavior determination does not indicate the exercise state" to the conditions for setting the pulse wave measurement to OFF, when the user continuously does exercise out of a predetermined time range or a predetermined place range, it is possible to continuously perform the pulse measurement. For example, when the user is in the exercise state within a range of position information (on path information) set as a running course, it is natural to determine that the user is running. Further, when the user continues the exercise state but the current position is out of the running course, it is not reasonable to determine that the running is terminated based on the current position. The reason is as follows. That is, as long as the user who is running continues the exercise state, it is natural to consider that the user is continuously running, and considering that the running may be widely performed at a place (for example, a sidewalk of a general road) which is not particularly designated as a running course, the fact that the position information does not satisfy its condition cannot become a ground for termination of the running. In this regard, by adding the above-described condition for setting the pulse wave measurement to OFF, it is possible to appropriately continue the pulse wave measurement while the user is continuously doing exercise.

Further, from another point of view, by considering the way of movement out of the position or path range, it is also possible to consider ON and OFF of the pulse measurement as different operations between when the user goes out of the designated range due to exercise and when the user goes out of the designated range due to non-exercise. For example, when the position information condition is not satisfied (the current position is out of the range of the position information or path information), and when the position or path is out of the range or it is determined that the movement is "movement by vehicle" in the behavior determination, the pulse wave measurement may be set to OFF.

As described above, even though the position state does not satisfy the condition, the pulse wave measurement may be continued as long as the exercise state is continued. In other words, if the user's behavior state is another state, a situation where the pulse wave measurement is necessary may not be continued. Particularly, when the position information condition is not satisfied due to the movement by vehicle, it is difficult to consider a situation where the user does exercise on the vehicle, for example, and thus, the pulse wave information is expected to be stable, similar to the resting state. That is, a timing when the current position moves by the "vehicle movement" from the inside of the range of the reference position to the outside of the range corresponds to a timing when the user's state is significantly changed, and thus, it is reasonable to consider that the pulse wave measurement is changed from a state where the necessity is high to a state where the necessity is low.

The determination regarding whether the movement is performed by the vehicle may be performed by various known techniques using acceleration or position information. Since these techniques may be widely applied in the present embodiment, detailed description thereof will not be made.

Further, in the determination using the schedule information, an example in which a predetermined user and another user may share or exchange the schedule information is described, but such a technique is not limited to the schedule information. Specifically, information relating to the determination using the amount of remaining battery, the behavior determination, and the determination using the position information, or information for regulating combinations thereof (determination table) may be shared by plural users.

For example, when a predetermined user A is associated with a user B different from the user A, and when the user A is close to the user B, ON or OFF of the pulse wave measurement of the activity state information detecting device 100 of the user A may be determined with reference to a determination table of the user B. Various techniques for associating the users may be used, but for example, when information indicating a close relationship is input by a user's input operation, users having the close relationship may be associated.

When the plural users having the close relationship are at close positions, a possibility that the respective users do not independently perform activities but are gathered for the purpose of doing the same activity in the plural users is high. In this case, it is considered that a situation where the necessity for pulse wave measurement is high for the user A and a situation where the necessity for pulse wave measurement is high for the user B are similar to each other. That is, the determination table of the user B may be applied to the user A, or the determination table of the user A may be applied to the user B, and thus, compared with a case where only a determination table for a single user is used, it is possible to perform a flexible determination process, for example.

4. Calculation Example of Activity State Information

As described above, when obtaining calorie consumption information as the activity state information, the calorie consumption information may be calculated based on the body motion information (first mode), or may be calculated based on the pulse wave information (second mode). Hereinafter, a technique for calculating calorie consumption information in each of the first and second modes will be described. Since the calculation technique of the calorie consumption information may employ various modification examples, calculation techniques other than the technique which will be described below may be used.

First, calorie consumption C (kcal) may be calculated by the following Expression (1). VO2 (ml/kg/min) in Expression (1) represents user's oxygen intake, W (kg) represents the weight of the user, and T (hour) represents a time indicating an activity period of time which is a calculation target of calorie consumption.

$$C = 0.3 \times VO2 \times W \times T \quad (1)$$

The weight W is known from user's personal information (setting information), and the time T may be determined if a period of time which is a calculation target is fixed. Accordingly, if the oxygen intake VO2 can be calculated, the calorie consumption C can be calculated. Hereinafter, a technique for calculating VO2 from acceleration and a technique for calculating VO2 from a pulse rate will be described.

When the acceleration is used, the oxygen intake VO2 is calculated by the following Expression (2).

$$VO2 = \text{oxygen intake due to exercise} + \text{oxygen intake due to resting metabolism} \quad (2)$$

Further, the oxygen intake due to exercise is 0.2×speed (m/min) during running, and 0.1×speed (m/min) during walking, which may be determined based on user's speed information.

The speed may be calculated by the following Expression (3) using body height H(m) and the number of steps S (steps/min). 0.4 in Expression (3) is a step width coefficient, and may be different values according to conditions. For example, since it is considered that the step width during running (for example, jogging) is larger than the step width during walking, the step width coefficient during walking may be set to 0.4 to 0.5, and the step width coefficient during jogging may be set to 0.5 to 0.7 or the like.

$$\text{Speed} = H \times 0.4 \times S \quad (3)$$

Here, it is known that the number of steps S may be calculated from the acceleration. For example, since the user periodically does exercise during walking or running, a signal cycle or frequency becomes information corresponding to the number of steps. When the activity state information detecting device 100 is mounted on the arm as shown in FIG. 5A, an acceleration signal becomes a signal corresponding to a swing of the arm, while one arm is swung back and forth once, the user walks by two steps, that is, one step by the right foot and one step by the left foot. In this case, two times the frequency of the acceleration signal becomes a walking frequency, and for example, if the value is magnified by 60 times, it is possible to calculate the number of steps per minute.

Various techniques for calculating the cycle or frequency of the acceleration signal may be considered. For example, a zero-cross point (point where a digital sample value is changed from a negative value to a positive value) of waveform of the acceleration signal may be detected. Alternatively, a peak (maximum value) of waveform of the acceleration signal may be detected, and when the maximum value exceeds a predetermined threshold value, the number of peaks may be counted as the number of steps. Further, a differential value (a difference between adjacent samples) of the acceleration signal may be calculated, and when a peak exceeds a predetermined threshold value, the number of peaks may be counted as the number of steps.

Further, a frequency conversion process may be performed for the acceleration signal. In this case, it is considered that waveform after the conversion process has, in addition to a basic frequency according to walking, characteristic frequency components having a high frequency relationship of two times or three times the basic frequency. Accordingly, such frequency components may be detected to calculate the number of steps for each predetermined time from the frequency components.

Further, the oxygen intake due to resting metabolism varies according to ages, sexes, and personal differences, but it is known that a value thereof is about 3 to 4. Accordingly, for example, the oxygen intake due to resting metabolism may be 3.5 (ml/kg/min).

Through the above-described process, the calorie consumption may be calculated from the acceleration. For example, if it is confirmed that S is 120 from the number of steps calculated using the acceleration signal, and that H is 1.7 from the user setting information, the speed becomes 1.7×0.4×120=81.6 (m/min) by Expression (3).

Further, if the weight of the user W is 50 and the user walks for an hour at the speed calculated above, VO2 becomes 0.1×81.6+3.5=11.66 by Expression (2), and thus, the calorie consumption C can be calculated as 0.3×11.66× 50×1=174.9 (kcal) by Expression (1).

As described above, the processing section 130 calculates the speed information (speed V) of the user based on the body motion information in the first mode, and calculates the calorie consumption information (calorie consumption C in a narrow sense) from the speed information. Specifically, the processing section 130 calculates information (the number of steps S) about the number of steps of the user based on the acceleration information which is body motion information in the first mode, calculates information about the user's speed based on the information about the number of steps, and calculates calorie consumption information which is activity state information from the speed information.

A technique for calculating the number of steps S from the acceleration may be any one of the various techniques described above, and Expression (3) may be used to calculate V from S. Further, since the oxygen intake VO2 may be calculated from the speed information V by Expression (2), the calorie consumption C may be calculated using Expression (1).

Next, a technique for calculating VO2 based on the pulse wave information and calculating the calorie consumption C will be described. In the present embodiment, when a pulse rate of a testee is represented as HR, a resting pulse rate which is a pulse rate during resting of the testee is represented as HRrest, and a maximum pulse rate defined as a function of the age of the testee is represented as HRmax, a relative pulse rate RHR is calculated by Expression (4).

$$RHR=(HR-HRrest)/(HRmax-HRrest)\times 100[\%] \quad (4)$$

In Expression (4), the maximum pulse rate HRmax may be defined by Expression (5). In Expression (5), AGE represents the age of the testee.

$$HRmax=220-AGE \quad (5)$$

Figure 8:
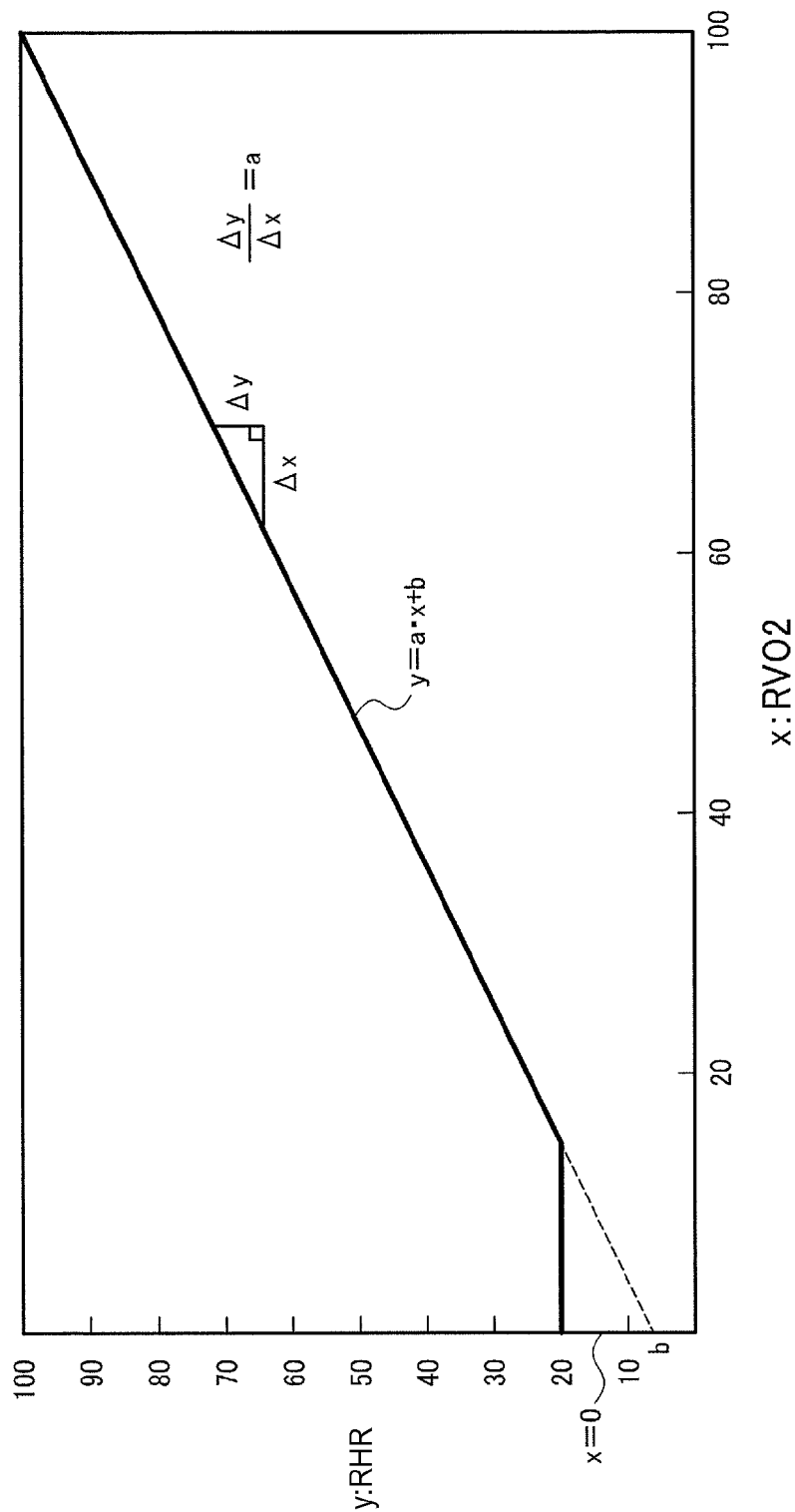
FIG. 8 is a diagram illustrating a relationship between a relative pulse rate and a relative oxygen intake.

It is known that a relative oxygen intake RVO2 may be calculated from the relative pulse rate RHR, but in the present embodiment, as shown in FIG. 8, the relative oxygen intake RVO2 is calculated by different expressions between when the relative pulse rate RHR is equal to or greater than 20% and when the relative pulse rate RHR is smaller than 20%. Here, a case where RHR is high corresponds to a case where exercise load is high, and a case where RHR is low corresponds to a case where exercise load is low.

The exemplified threshold value is determined in consideration of a point called AT. An anaerobic metabolism threshold (AT) refers to oxygen intake (VO2) at a point of time when anaerobic metabolism starts in addition to aerobic metabolism, which is a maximum exercise level capable of being relatively safely continued for a long period of time.

More specifically, when the relative pulse rate RHR is equal to or greater than 20% (when exercise load is high), and when an inclination of an approximation straight line y indicating the relationship between the relative pulse rate RHR (y-axis) and the relative oxygen intake RVO2 (x-axis), calculated by a test in advance, is represented as a and a segment of the approximate straight line y on the axis (y-axis) corresponding to the relative pulse rate RHR is represented as b, the relative oxygen intake RVO2 is calculated by the following Expression (6). On the other hand, when the relative pulse rate RHR is smaller than 20% (when exercise load is low), the relative oxygen intake RVO2 is calculated by the following Expression (7).

$$RVO2=(RHR-b)/a \quad (6)$$

$$RVO2=0 \quad (7)$$

This is because in a state where the relative pulse rate RHR is low, an error becomes large due to low reliability of the pulse rate. However, in this area, even though the error of the relative pulse rate RHR is large to some extent, since the error does not noticeably affect the calculation of the relative oxygen intake ROV2, the above-mentioned Expression (7) which is obtained by a test and is easily handled is defined as a calculation expression.

Next, the relationship between the relative oxygen intake RVO2 and the oxygen intake VO2 will be described. In the present embodiment, when a maximum oxygen intake is represented as VO2max and a resting oxygen intake which is a basic metabolic rate is represented as VO2rest, the oxygen intake VO2 is defined by the following Expression (8). Here, it is assumed that the maximum oxygen intake VO2max is input and set by a user in advance. Further, the resting oxygen intake VO2rest in the following Expression (8) may be calculated using the Harris Benedict equation, for example. Here, a value of VO2rest may be converted into a value per minute as necessary for unifying units.

$$VO2=RVO2\times(VO2max-VO2rest)+VO2rest \quad (8)$$

That is, when the pulse rate HR is calculated as pulse wave information, the oxygen intake VO2 can be calculated by using Expressions (4) to (8). Further, if VO2 can be calculated, the calorie consumption C can be calculated by the Expression (1).

5. Specific Example of Process in Second Mode

In the above description, when calculating the activity state information, the technique for switching the first mode using the body motion information and the second mode using the pulse wave information is described. When the second mode is set by this technique, the activity state information detecting device 100 may acquire both of the body motion information and the pulse wave information.

Accordingly, in the following description, a specific example of a process using the body motion information and the pulse wave information, that is, a process in the second mode will be described.

In the present embodiment, for example, a sleep state of a user may be determined using change information on the body motion information and change information on the pulse wave information. As described above, in determination using only the body motion information, it is difficult to distinguish between the sleep state and the resting state in a state of being awake.

In this regard, the pulse wave information is information that reflects various internal activities of a user, and for example, it is known that a pulse rate increases in a mental activity state such as thinking, or in a state where the user feels mental stress (even though a physical motion is small).

In a state of being awake, the user performs various physical and mental activities, but in the sleep state, most activities are suppressed, except for activities for maintaining a biological activity (life activity). That is, since the pulse wave information reflects an internal activity state, if the pulse rate is high, it may be determined that the user is in a state of being awake, and if the pulse rate is low, it may be determined that the user is in the sleep state. Thus, it is possible to determine the sleep state or the state of being awake based on fundamental determination relating to the activity states of the user.

However, as a test result of the present inventors, it was found that the determination result of the sleep state using the pulse wave information may not be suitable for user's bodily sensation. For example, ideally, it is considered that when a user transitions from the state of being awake to the sleep state, the pulse rate decreases by a certain width, but in reality, there is a case where it takes time until the pulse rate decreases after the user transitions to the sleep state, or a case where even though the user transitions to the sleep state, the pulse rate does not sufficiently decrease and the user re-transitions to the state of being awake.

As a specific situation, a case where the user drinks alcohol before sleeping may be considered. Since the alcohol should be decomposed in the body, an activity for the alcohol decomposition is essential. That is, even though the user transitions to the sleep state, the activity is performed while the alcohol is being decomposed, and the pulse wave information reflects the activity. Thus, the pulse rate does not drop.

As another example, an apnea or hypopnea situation such as a sleep apnea syndrome may be considered. In the apnea or hypopnea situation, a user's blood oxygen concentration (arterial oxygen saturation SpO2) drops, and when the apnea or the like is eliminated, it is necessary to activate an activity for recovering the dropped SpO2 to a normal state. That is, there may be a case where the pulse rate does not drop even in the sleep state due to such a disease.

Further, there is a case where the pulse rate does not drop as a predetermined activity is performed even though the user is in the sleep state. In this case, a result of a state of being awake is acquired in determination using the pulse rate. Here, if it is interpreted that the sleep state refers to a state where the user's activity is suppressed so that it is valuable for the user to take a rest, a period of time when the pulse rate does not drop may not be considered as the sleep state. This is because in a state where various activities such as the above-described alcohol decomposition or recovery from the drop of SpO2 are performed, the user does not sufficiently take a rest.

However, since it is difficult for the user to recognize the internal activity, the determination result regarding the sleep state or the state of being awake based on the above-mentioned definition is quite distant from the user's own sense. That is, from a standpoint of the user, the sleep state refers to a sleep state which is a resting state and is generally called a state where the consciousness level (and response to external stimuli) drops. Further, even though the activity for the alcohol decomposition is performed in such a general sleep state, it is natural to determine the state as the sleep state, and it is not preferable to determine the state as the state of being awake.

In consideration of the above-described points, it is considered that it is not sufficient to use only one of the body motion information and the pulse wave information in the determination of the sleep state. Further, the determination using both of the body motion information and the pulse wave information is performed in the related art, but it is not sufficient to perform the determination with only a combination of threshold value determination based on the body motion information and a predetermined body motion threshold value and threshold value determination based on the pulse wave information and a predetermined pulse wave threshold value. For example, if a technique for determining that a user is in a sleep state in a case where an acceleration value is lower than a predetermined acceleration threshold value and a pulse rate is lower than a predetermined pulse rate threshold value is used, in an example shown in FIG. 9A, since an acceleration condition is satisfied at a timing A1 and a pulse rate condition is satisfied at a timing A2, it is determined that the sleep state is started at the timing A2. In this case, there is a possibility that the sleep state starts from the timing A1, and in a period from the timing A1 to the timing A2, the pulse rate does not drop due to the above-described various causes even in the sleep state. That is, in the period from the timing A1 to the timing A2, although it cannot be said that the user is in the sleep state, and that the user is in the resting state in a state of being awake, it is determined that the user is in a state of being awake without distinction.

Thus, in the determination technique of the sleep state using both of the body motion information and the pulse wave information, the inventors propose a technique that employs a change tendency of the body motion information and the pulse wave information over a predetermined period of time, instead of determination at a predetermined timing (sequential determination). Specifically, the processing section 130 of the activity state information detecting device 100 according to the present embodiment performs the determination of the sleep state of the user based on change information on the pulse wave information and change information on the body motion information over a predetermined period of time in the second mode.

Figure 9A:
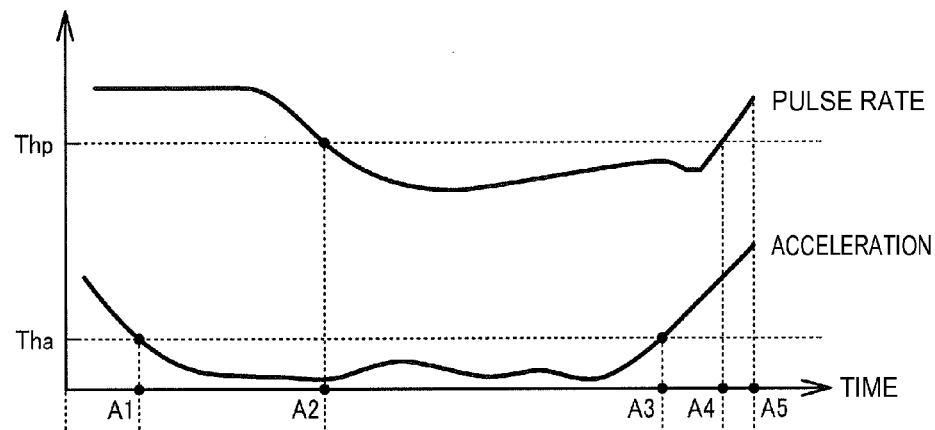
FIG. 9A is a diagram illustrating a specific example of pulse wave information and body motion information.
Figure 9B:
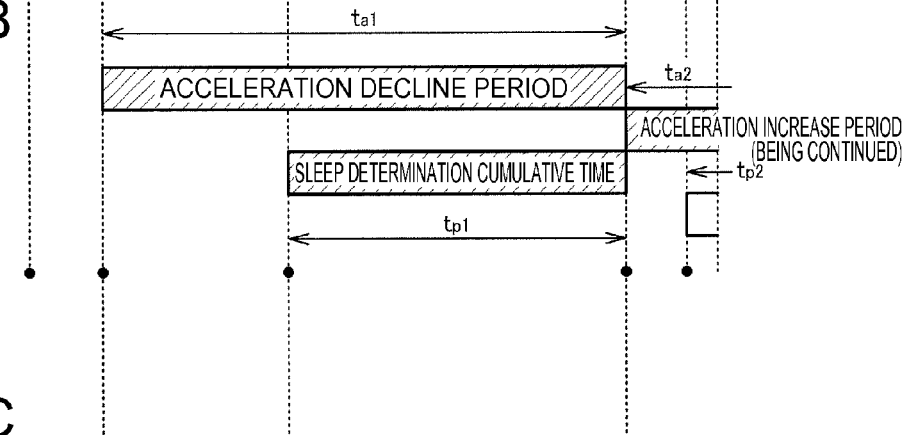
FIGS. 9B and 9C are diagrams illustrating a sleep state determination process in a second mode.
Figure 9C:
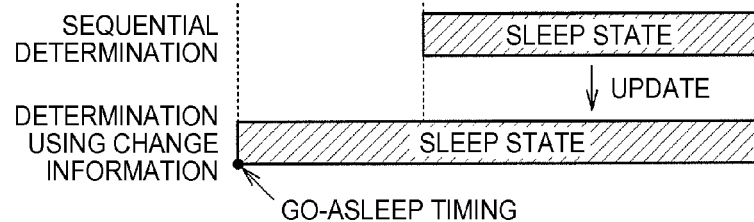

With such a configuration, differently from the sequential determination using the body motion information and the pulse wave information at the predetermined timing, it is possible to use the body motion information and the pulse wave information in the determination over a certain period of time. In the example shown in FIG. 9A, the pulse rate drops at the timing A2 which is delayed to some extent with respect to the timing A1 at which it may be considered that the user transitions to the sleep state. In this case, the pulse rate drops at the timing A2 which is delayed with respect to the timing A1, and the drop is shown over a certain period of time. Further, decline of acceleration at the timing A1 and thereafter is continued over a long period of time. All these tendencies may be bases for determining that a physical activity suppression period (acceleration decline period) started from the timing A1 indicates the sleep state. That is, the acceleration decline period may be estimated to indicate the sleep state other than the resting state in a state of being awake. As shown in FIG. 9C, in the sequential determination at the timing A1, it is difficult to determine that the timing A1 indicates the start of the sleep state, but if the body motion information and the pulse wave information are continuously observed from the timing A1 to at least the timing A2 and thereafter, determination of going back to the past at the timing A2 and thereafter may be performed. That is, it may be determined again that the timing A1 is the start timing of the sleep state.

The change information on the body motion information in the present embodiment represents the acceleration decline period or a length thereof or an acceleration increase period or a length thereof in a narrow sense, and the change information on the pulse wave information represents a sleep determination cumulative time. Here, the change information is not limited thereto, and may be different information calculated based on temporal changes in the body motion information and the pulse wave information.

Hereinafter, a specific example of the process will be described. In the second mode, the processing section 130 calculates an acceleration decline period when it is determined that an acceleration is continuously lower than an acceleration threshold value Tha based on the change information on the body motion information, calculates a sleep determination cumulative time which is a cumulative value of a period of time when it is determined that a pulse rate in the acceleration decline period is lower than a pulse rate threshold value Thp based on the change information on the pulse wave information, and performs determination of the sleep state based on the acceleration decline period and the sleep determination cumulative time.

That is, the processing section 130 monitors a temporal change in the acceleration, and stores a timing when the acceleration is lower than the acceleration threshold value Tha as a go-asleep timing candidate. Further, while the acceleration is continuously lower than the acceleration threshold value Tha, a continuous time of the acceleration decline period is continuously calculated. In addition, during the acceleration decline period, a temporal change in the pulse rate is also checked. Specifically, when the pulse rate is lower than the pulse rate threshold value Thp and it is determined that the period indicates the sleep state, the sleep determination cumulative time is continuously calculated. That is, in the present embodiment, similarly, it is assumed that the determination process using the acceleration and the acceleration threshold value Tha and the determination process using the pulse rate and the pulse rate threshold value Thp are sequentially performed.

Through the above-described processes, it is possible to calculate a length ta1 of the acceleration decline period, and a length tp1 of the sleep determination cumulative time during the acceleration decline period. Here, it is considered that the acceleration decline period appears plural times. In the present embodiment, the length ta1 and the length tp1 of the corresponding sleep determination cumulative time are calculated with respect to each of the plural acceleration decline periods. The acceleration decline period and the length ta1 thereof and the sleep determination cumulative time tp1 in the example of FIG. 9A are shown in FIG. 9B. In FIG. 9A, an example in which the sleep determination cumulative time tp1 is represented as a time indicating the length of one continuous period is described, but in a case where the period when the pulse rate is lower than the pulse rate threshold value Thp appears plural times during one acceleration decline period, a cumulative value of the respective periods may be represented as tp1.

After calculation of the length ta1 of the acceleration decline period and the sleep determination cumulative time tp1, when it is determined that the sleep determination cumulative time tp1 is equal to or greater than a pulse cumulative time threshold value Thtp, the processing section 130 performs the determination of the sleep state by threshold value determination using the length ta1 of the acceleration decline period and a first acceleration cumulative time threshold value Thta1. Specifically, when ta1 is equal to or greater than Thta1 and tp1 is equal to or greater than Thtp, it is determined that the corresponding acceleration decline period indicates the sleep state, and a timing stored as the go-asleep timing candidate, that is, a start timing of the acceleration decline period is used as a go-asleep timing.

In the example of FIG. 9A, in a stage where the sequential determination is performed as shown in FIG. 9C, since it is determined that the timing A2 is a go-asleep timing, it is possible to update the go-asleep timing from the timing A2 to the timing A1 using the technique of the present embodiment.

Here, the first acceleration cumulative time threshold value Thta1 is about 30 minutes, for example, and the pulse cumulative time threshold value Thtp is about 10 minutes, for example. The first acceleration cumulative time threshold value Thta1 is used for the determination under the assumption that the sleep state is continued for a certain period of time. That is, in a case where the length ta1 of the acceleration decline period is smaller than the first acceleration cumulative time threshold value Thta1, it is determined that the acceleration decline time is too short, and thus, it is not determined that the period is the sleep state.

Further, with respect to the pulse rate, a period when the pulse rate does not drop even in the sleep state (a period which does not contribute to the sleep determination cumulative time tp1) as in the period from the timing A1 to the timing A2 in FIG. 9A may be present, and it is considered that the pulse rate drops over a certain amount of period in the sleep state. Further, even though the pulse rate drops in an extremely short period (at a predetermined timing as an extreme example), this may be an erroneous determination due to noise or the like. Accordingly, here, the determination using the pulse cumulative time threshold value Thtp is performed.

Through the above-described processes, in the case shown in FIG. 9A, it is possible to appropriately determine a go-asleep timing. However, there is a case where it is not possible to appropriately determine the sleep state only using the above-described determination. Specifically, there is a case shown in FIG. 10A. As described above, in the case of alcohol intake or when a disease such as sleep apnea occurs, the pulse rate does not sufficiently drop. Here, when the intake of alcohol is excessively large, or when the sleep apnea continuously appears in the sleep state, since a certain activity is continuously performed in the sleep state, the pulse rate may do not sufficiently drop at any timing in the sleep state as shown in FIG. 10A.

Figure 10A:
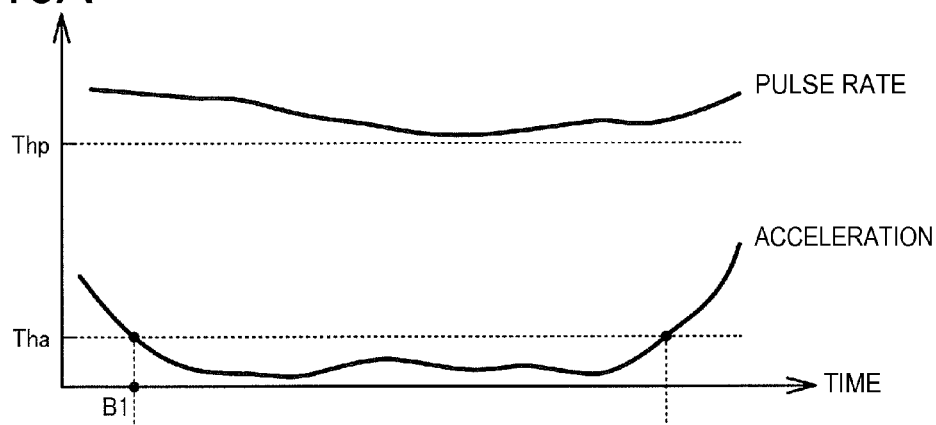
FIGS. 10A to 10C are diagrams illustrating a process example with respect to a user whose pulse rate is not reduced.
Figure 10B:
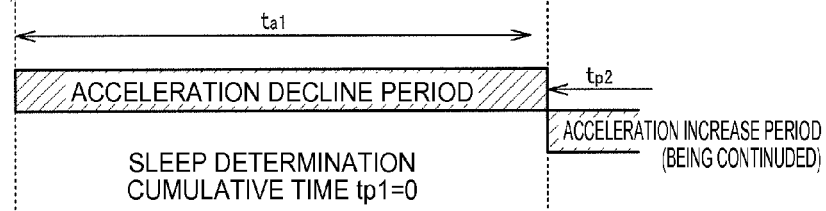

In this case, as shown in FIG. 10B, it is possible to detect the acceleration decline period, and to calculate the length tat, but the sleep determination cumulative time tp1 corresponding to the acceleration decline period becomes 0. Thus, since the condition of tp1≥Thtp is not satisfied in the determination, it cannot be determined that the period indicates the sleep state. However, even in such a state, since the user is actually in the sleep state, it is preferable to determine that the acceleration decline period indicates the sleep state.

Accordingly, in the present embodiment, the processing section 130 may determine a determination condition in the determination of the sleep state using the change information on the body motion information, based on the change information on the pulse wave information. Specifically, if the pulse rate during the acceleration decline period sufficiently drops, the determination may be performed under the above-described determination condition, and if the drop of the pulse rate is not sufficient, the determination may be performed under other conditions.

With such a configuration, even in the case shown in FIG. 10A, it is possible to make a room for determining that the acceleration decline period indicates the sleep state, that is, for determining that the go-asleep timing candidate is the go-asleep timing, and it is possible to perform sleep state determination suitable for the user's bodily sense.

However, when the drop of pulse rate is not sufficient, there is a case where it is considered that the user is not in the sleep state in the determination using the change information on the pulse wave information. Thus, when the determination of the sleep state is performed using the change information on the body motion information, it is not preferable to use a loosened condition (condition that it is easily determined that the user is in the sleep state). In other words, as long as a feeling that the user is not in the sleep state in the determination using the change information on the pulse wave information is obtained, in order to confirm that the final determination indicates the sleep state while ignoring the feeling, it is necessary to obtain a result which can become a basis of strong estimation that the user is in the sleep state from the change information on the body motion information.

Accordingly, when a change width of the change information on the pulse wave information is a first change width, the processing section 130 may perform the determination of the sleep state using the change information on the body motion information according to a first determination condition, and when the change width of the change information on the pulse wave information is a second change width which is smaller than the first change width, the processing section 130 may perform the determination of the sleep state using the change information on the body motion information according to a second determination condition that it is difficult to determined that the user is in the sleep state compared with the first determination condition. In other words, when the change width of the change information on the pulse wave information is large, the processing section 130 performs the determination of the sleep state using the change information on the body motion information according to the first determination condition, and when the change width of the change information on the pulse wave information is small, the processing section 130 performs the determination of the sleep state using the change information on the body motion information according to the second determination condition. The first change width and the second change width may be determined by a comparison process with respect to a predetermined change width threshold value, for example. In this case, in an example in which a difference between a maximum value and a minimum value is used as the change width, the first change width represents a case where the difference between the maximum value and the minimum value is equal to or greater than the change width threshold value, and the second change width represents a case where the difference between the maximum value and the minimum value is smaller than the change width threshold value.

It is considered that the pulse rate threshold value Thp is a value based on a pulse rate (for example, a lowest pulse rate) which is measured by a user who is a target. That is, in a narrow sense, the change width represents a decline width (difference) of the value with reference to the maximum value, but the pulse rate threshold value Thp may be used as a reference when calculating the change width. For example, the change width may be calculated from the decline width of the pulse rate with reference to the pulse rate threshold value Thp.

Specifically, when it is determined that the sleep determination cumulative time tp1 is smaller than the pulse cumulative time threshold value Thtp, the processing section 130 performs the determination of the sleep state by threshold value determination using the second acceleration cumulative time threshold value Thta2 which is a value larger than the first acceleration cumulative time threshold value Thta1 and the length ta1 of the acceleration decline period. More specifically, in the case of tp1<Thtp, when the condition of ta1≥Thta2 (>Thta1) is satisfied, it may be determined that the user is in the sleep state. That is, in this case, the first determination condition represents whether or not the condition of ta1≥Thta1 is satisfied, or the second determination condition represents whether or not the condition of ta1≥Thta2 is satisfied. As described above, since the second acceleration cumulative time threshold value Thta2 is greater than the first acceleration cumulative time threshold value Thta1, the second determination condition is stricter than the first determination condition.

Figure 10C:
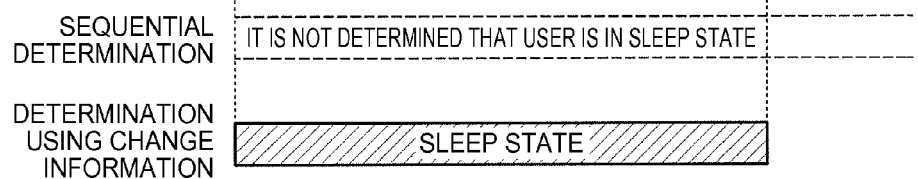

Here, the second acceleration cumulative time threshold value Thta2 is about 3 hours, for example. Then, in the case of FIG. 10A, since the sleep determination cumulative time tp1 is 0 as shown in FIG. 10B, it is not possible to satisfy the condition of tp1≥Thtp and the condition of ta1≥Thta1, but since the condition of ta1≥Thta2 is satisfied, that is, since the length of the acceleration decline period is very long, it is possible to consider the acceleration decline period as the sleep state, and to determine a timing B1 as a go-asleep timing. That is, as shown in FIG. 10C, it is possible to appropriately perform the determination of the sleep state.

With respect to the second acceleration cumulative time threshold value Thta2, it is preferable to set a time which is considered as a continuous time of the resting state in a state of being awake. In a state of being awake, it may be considered that the acceleration decline period is interrupted due to change in the user's posture or going to the bathroom, but in the sleep state, the acceleration decline period is continued over a long period of time such as 6 hours to 8 hours. Here, it is preferable to set the second acceleration cumulative time threshold value Thta2 to a time such that these two states can be distinguished.

Figure 11A:
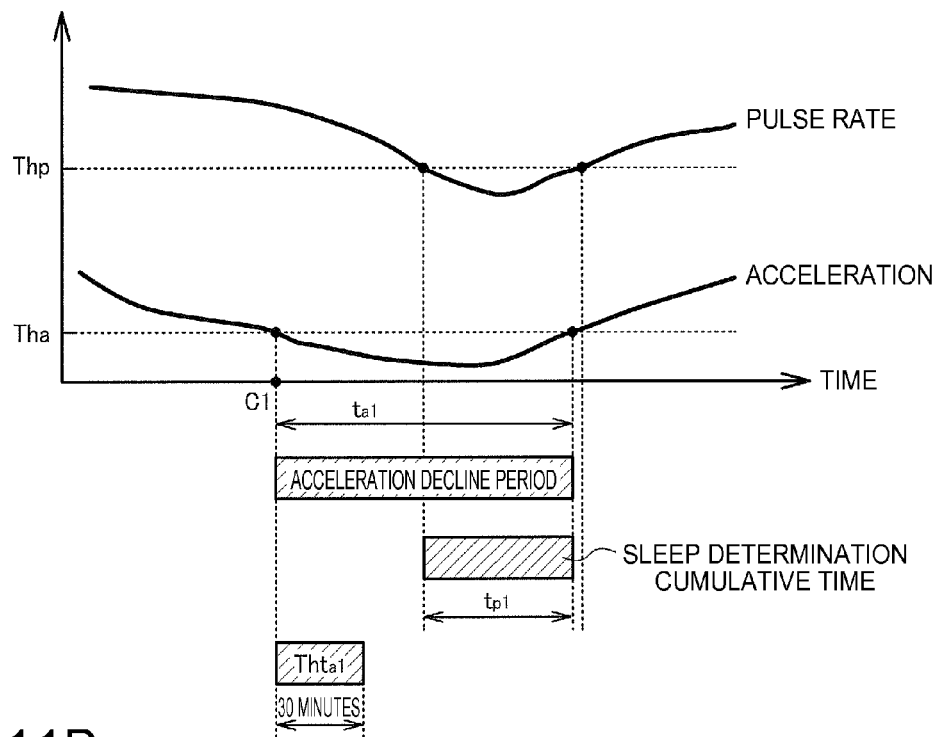
FIGS. 11A and 11B are diagrams illustrating a process of changing a threshold value according to a sleep determination cumulative time.
Figure 11B:
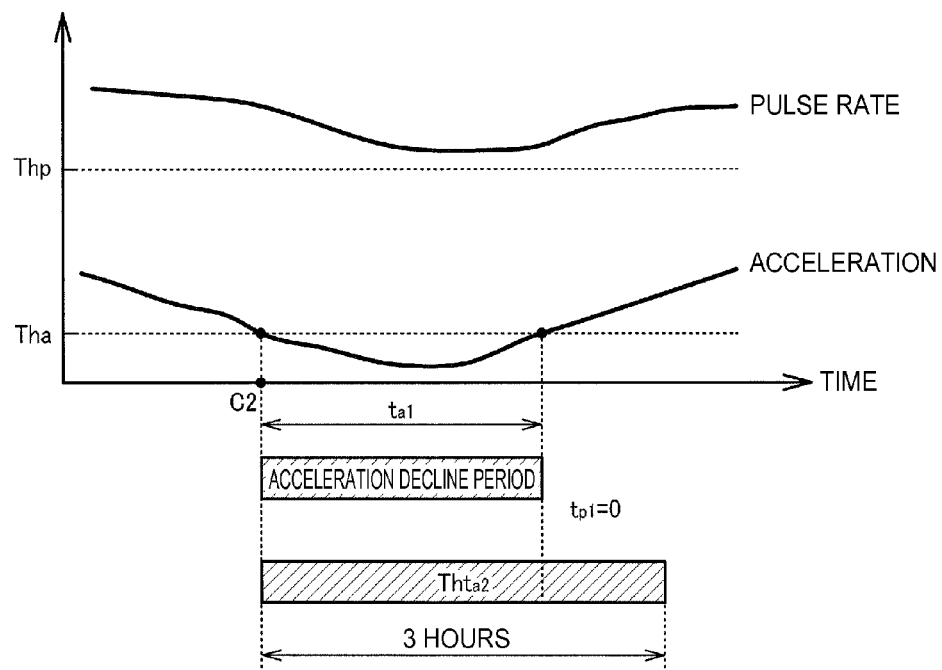

In this way, since there are two determination conditions, even when the length ta1 of the acceleration decline period is the same, the determination result may be changed according to the length of the sleep determination cumulative time tp1. Specific examples thereof are shown in FIGS. 11A and 11B. In both cases, the length ta1 of the acceleration decline period is set to 2 hours. Since the condition of tp1≥Thtp is satisfied in FIG. 11A, a comparison target with reference to the length ta1 of the acceleration decline period is the first acceleration cumulative time threshold value Thta1=30 minutes. Thus, the condition of ta1≥Thta1 is satisfied, and thus, it can be determined that a timing C1 is a go-asleep timing. On the other hand, since the condition of tp1≥Thtp is not satisfied in FIG. 11B, a comparison target with reference to the length ta1 of the acceleration decline period is the second acceleration cumulative time threshold value Thta2=3 hours. Thus, the condition of ta1≥Thta2 is not satisfied, and thus, it is not determined that a timing C2 is a go-asleep timing.

Further, in the above description, the start timing (go-asleep timing) in the determination of the sleep state is described, but the same process may be performed for an end timing (wake-up timing). Further, the determination process of the sleep state in the second mode is not limited to the above description, and other determination processes may be performed. Furthermore, the process performed in the second mode is not limited to the determination process of the sleep state, and other processes may be performed.

Hereinabove, the embodiments have been described in detail, but those skilled in the art will understand that various modifications can be made in a range without substantially departing from novel matters and effects of the invention. Accordingly, all these modifications are included in the scope of the invention. For example, a term which is used at least once in the description and the drawings together with a different term having a wider meaning or the same meaning may be replaced with the different term in any location of the description and the drawings. Further, the configuration and the operation of the activity state information detecting device are not limited to those described in the present embodiment, and various modifications may be used.

What is claimed is:

1. An activity state information detecting device comprising:
    a pulse wave measuring section that measures pulse wave information of a user;
    a body motion measuring section that measures body motion information of the user; and
    a processing section that performs a calculation process of activity state information of the user,
    wherein the processing section performs a mode switching process between a first mode for performing the calculation process of the activity state information based on the body motion information and a second mode for performing the calculation process of the activity state information based on the pulse wave information.

2. The activity state information detecting device according to claim 1,
    wherein the processing section performs the mode switching process based on an amount of remaining battery.

3. The activity state information detecting device according to claim 2,
    wherein the processing section sets the second mode when the amount of remaining battery is equal to or greater than a predetermined threshold value, and sets the first mode or the second mode when the amount of remaining battery is smaller than the predetermined threshold value.

4. The activity state information detecting device according to claim 3,
    wherein when the amount of remaining battery is smaller than the predetermined threshold value, and when it is determined that the user is in an exercise state or a sleep state based on the body motion information, the processing section sets the second mode.

5. The activity state information detecting device according to claim 3,
    wherein when the amount of remaining battery is smaller than the predetermined threshold value, and when it is determined that the user is in a resting state based on the body motion information, the processing section sets the first mode.

6. The activity state information detecting device according to claim 1,
    wherein when it is determined that the user is in an exercise state or a sleep state based on the body motion information, the processing section sets the second mode.

7. The activity state information detecting device according to claim 1,
    wherein when it is determined that the user is in a resting state based on the body motion information, the processing section sets the first mode.

8. The activity state information detecting device according to claim 1,
    wherein the processing section performs the mode switching process based on at least one of schedule information and timing information.

9. The activity state information detecting device according to claim 8,
    wherein when it is determined that the user is in an exercise state or a sleep state based on at least one of the schedule information and the timing information, the processing section sets the second mode.

10. The activity state information detecting device according to claim 1, further comprising:
    a position information acquiring section that acquires position information of the user,
    wherein the processing section performs the mode switching process based on the position information.

11. The activity state information detecting device according to claim 10,
    wherein when it is determined that the user is in an exercise state based on the position information, the processing section sets the second mode.

12. The activity state information detecting device according to claim 1,
    wherein the processing section calculates calorie consumption information as the activity state information based on the body motion information in the first mode, and calculates the calorie consumption information as the activity state information based on the pulse wave information in the second mode.

13. The activity state information detecting device according to claim 12,
    wherein the processing section calculates speed information of the user based on the body motion information in the first mode, and calculates the calorie consumption information from the speed information.

14. The activity state information detecting device according to claim 13,
    wherein the processing section calculates step number information of the user based on acceleration information which is the body motion information in the first mode, calculates the speed information of the user based on the step number information, and calculates the calorie consumption information as the activity state information from the speed information.

15. A method for controlling an activity state information detecting device, the method comprising:
    measuring pulse wave information of a user;
    measuring body motion information of the user;
    performing a mode switching process between a first mode for performing a calculation process of activity state information based on the body motion information and a second mode for performing the calculation process of the activity state information based on the pulse wave information; and
    performing the calculation process of the activity state information in a mode set in the mode switching process.

* * * * *